United States Patent
Hoogi et al.

(10) Patent No.: US 10,420,523 B2
(45) Date of Patent: Sep. 24, 2019

(54) ADAPTIVE LOCAL WINDOW-BASED METHODS FOR CHARACTERIZING FEATURES OF INTEREST IN DIGITAL IMAGES AND SYSTEMS FOR PRACTICING SAME

(71) Applicant: The Board of Trustees of the Leland Stanford Junior University, Stanford, CA (US)

(72) Inventors: Assaf Hoogi, Mountain View, CA (US); Daniel L. Rubin, Stanford, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 132 days.

(21) Appl. No.: 15/465,459

(22) Filed: Mar. 21, 2017

(65) Prior Publication Data
US 2017/0270664 A1 Sep. 21, 2017

Related U.S. Application Data

(60) Provisional application No. 62/311,058, filed on Mar. 21, 2016.

(51) Int. Cl.
*A61B 6/00* (2006.01)
*A61B 5/055* (2006.01)
(Continued)

(52) U.S. Cl.
CPC ............ *A61B 6/5217* (2013.01); *A61B 5/055* (2013.01); *A61B 6/032* (2013.01); *A61B 6/502* (2013.01); *G06T 7/10* (2017.01); *G06T 7/12* (2017.01); *G06T 7/174* (2017.01); *G06T 7/194* (2017.01); *A61B 5/725* (2013.01); *A61B 5/7267* (2013.01); *G06T 2207/10081* (2013.01); *G06T 2207/10088* (2013.01); *G06T 2207/10116* (2013.01);
(Continued)

(58) Field of Classification Search
None
See application file for complete search history.

(56) References Cited

U.S. PATENT DOCUMENTS 6,366,684 B1    4/2002   Gerard et al.
6,803,920 B2   10/2004   Gossett et al.
(Continued)

OTHER PUBLICATIONS

An et al. (2007) "Convergence approximation to piecewise smooth medical image segmentation" Proc. Med. Imag. Comput. Comp. Assist. Interven., 4792:495-502.
(Continued)

*Primary Examiner* — Idowu O Osifade
(74) *Attorney, Agent, or Firm* — Brian E. Davy; Bozicevic, Field & Francis LLP

(57) ABSTRACT

Provided are methods for characterizing a feature of interest in a digital image. In certain aspects, the methods use an adaptive local window and include obtaining an initial contour for a feature of interest, defining a region of interest around the contour, and segmenting the feature of interest by iteratively selecting a size of a local window surrounding each point on the contour. Non-transitory computer readable media and systems that find use in practicing the methods of the present disclosure are also provided.

20 Claims, 16 Drawing Sheets

(51) Int. Cl.

| | | |
|---|---|---|
| *A61B 6/03* | (2006.01) | |
| *G06T 7/10* | (2017.01) | |
| *G06T 7/12* | (2017.01) | |
| *G06T 7/174* | (2017.01) | |
| *G06T 7/194* | (2017.01) | |
| *A61B 5/00* | (2006.01) | |

(52) U.S. Cl.
CPC .............. *G06T 2207/20016* (2013.01); *G06T 2207/20081* (2013.01); *G06T 2207/20084* (2013.01); *G06T 2207/20104* (2013.01); *G06T 2207/30096* (2013.01)

(56) References Cited

U.S. PATENT DOCUMENTS

| 7,747,070 B2 | 6/2010 | Puri | |
|---|---|---|---|
| 9,082,165 B2 | 7/2015 | Guissin et al. | |
| 2015/0078640 A1* | 3/2015 | Guo | G06T 7/149 382/131 |

OTHER PUBLICATIONS

Arbelaez et al. (2010) "Contour Detection and Hierarchical Image Segmentation" IEEE Transactions on Image Processing; p. 1-20.

Baillard et al. (2000) "Robust adaptive segmentation of 3-D medical images with level sets" IRISA, Rennes Cedex, France, Res. Rep. 1369.

Chan and Vese (2001) "Active Contours Without Edges" IEEE Transactions on Image Processing; 10(2):266-277.

Glorot and Bengio (2010) "Understanding the difficulty of training deep feedforward neural networks" in Proc. AISTATS, 249-256.

Haralick et al. (1973) "Textural Features for Image Classification" IEEE Transactions on Systems, Man and Cybernetics, SMC 3(6):610-620.

Hinton et al. (2012) "Improving neural networks by preventing co-adaptation of feature detectors" arXiv preprint arXiv:1207.0580.

Hoogi et al. (2016) "Adaptive Local Window for Level Set Segmentation of CT and MR Liver Lesions" IEEE Transactions on Image Processing; p. 1-11.

Hoogi et al. (2016) "Learning of Active Contours Parameters Using Convolutional Neural Network" IEEE Transactions on Image Processing; p. 1-10.

Krizhevsky et al. (2012) "ImageNet Classification with Deep Convolutional Neural Networks" Advances in Neural Information Processing Systems, 9 pgs.

Lankton et al. (2007) "Hybrid geodesic region-based curve evolutions for image segmentation" in Proc. SPIE: Med. Imag., 6510:65104U, 10 pgs.

Lankton and Tannenbaum (2008) "Localizing region-based active Contours" IEEE Trans.Image Process, 17(11):2029-2039.

Li et al (2007) "Implicit active contours driven by local binary fitting energy" in: IEEE Conference on Computer Vision and Pattern Recognition, 9 pgs.

Li et al. (2008) "Minimization of region-scalable fitting energy for image segmentation" IEEE Transactions on Image Processing, 17(10):1940-1949.

Li et al. (2009) "Integrating FCM and level sets for liver tumor Segmentation" Proceedings, 23:202-205.

Malladi et al. (1994) "Shape modeling with front propagation: a level set approach" IEEE Transaction on Pattern Analysis and Machine Intelligence, 17:158-175.

Oliveira et al. (2009) "Liver Segmentation using Level Sets and Genetic Algorithms" 4th Visapp. 2:154-159.

Piovano and Papadopoulo (2008) "Local statistics based region segmentation with automatic scale selection" ECCV, Part 11, LNCS 5303:486-499.

Smeets et al. (2008) "Segmentation of liver metastases using a level set method with spiral-scanning technique and supervised fuzzy pixel classification" 3D Segmentation in the Clinic: A Grand Challenge II—Liver Tumor Segmentation, 12 pgs.

Wang et al. (2009) "Level set segmentation based on local Gaussian distribution fitting" Asian Conference on Computer Vision, 293-302.

Yang and Boukerroui (2011) "Optimal spatial adaptation for local region-based active contours: An intersection of confidence intervals approach" IMAGAPP, 87-93.

Yezzi et al. (2002) "A fully global approach to image segmentation via coupled curve evolution equations" J. Vis. Comm. Image Rep., 13(1):195-216.

Zhang et al. (2010) "Active contours driven by local image fitting energy" Pattern Recognit., 43(4):1199-1206.

Zheng et al. (2013) "A robust medical image segmentation model using KL distance and local neighborhood information" Computers in Biol. and Med., 43(5):459-470.

\* cited by examiner

11A

11B

11C

11D

11E

11F

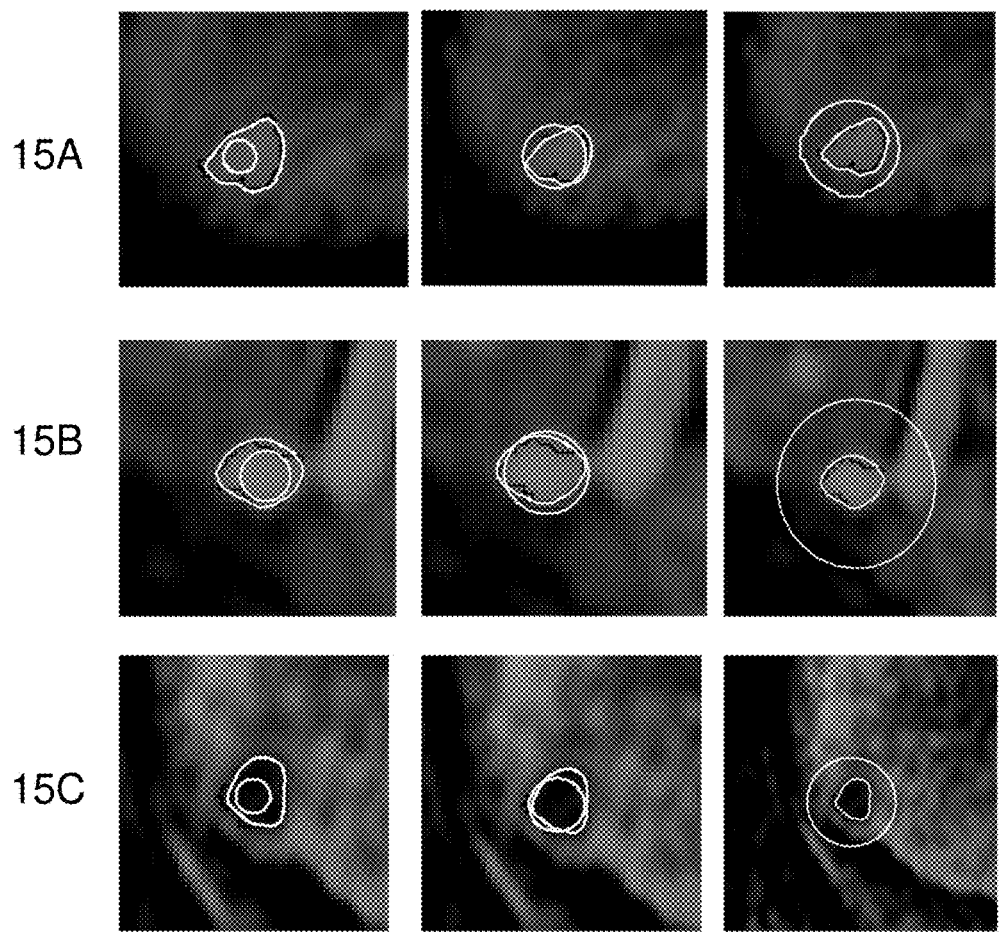
Figure 15A, B, C

ADAPTIVE LOCAL WINDOW-BASED METHODS FOR CHARACTERIZING FEATURES OF INTEREST IN DIGITAL IMAGES AND SYSTEMS FOR PRACTICING SAME

CROSS-REFERENCE TO RELATED APPLICATIONS

This application claims the benefit of U.S. Provisional Patent Application No. 62/311,058 filed Mar. 21, 2016, which application is incorporated herein by reference in its entirety.

STATEMENT OF GOVERNMENTAL SUPPORT

This invention was made with Government support under contracts CA142555 and CA190214 awarded by the National Institutes of Health. The Government has certain rights in the invention.

BACKGROUND OF THE INVENTION

Field of the Invention

The present invention relates to the field of imaging analysis, in particular to methods for analyzing digital images of clinical samples in a computerized method to determine boundaries of a feature of interest, such as a lesion in an MRI or CT scan. The invention also has non-medical applications.

Related Art

Presented below is background information on certain aspects of the present invention as they may relate to technical features referred to in the detailed description, but not necessarily described in detail. That is, individual compositions or methods used in the present invention may be described in greater detail in the publications and patents discussed below, which may provide further guidance to those skilled in the art for making or using certain aspects of the present invention as claimed. The discussion below should not be construed as an admission as to the relevance or the prior art effect of the patents or publications described.

In computer vision, image segmentation involves automated outlining of the boundaries of the object in the image. The goal of segmentation is to simplify and/or change the representation of an image into something that is more meaningful and easier to analyze. Image segmentation is typically used to locate objects and boundaries (lines, curves, etc.) in images. More precisely, image segmentation is the process of assigning a label to every pixel in an image such that pixels with the same label share certain characteristics.

The result of image segmentation is a set of segments that collectively cover the features of interest, or a set of contours extracted from the image (see edge/region detection). Each of the pixels in a region is similar with respect to one or more spatial characteristic or computed property, such as color, intensity, or texture. Adjacent regions are significantly similar with respect to the same characteristic(s). When applied to a stack of images, typical in medical imaging, the resulting contours after image segmentation can be used to create 3D reconstructions with the help of interpolation algorithms like marching cubes. (https (colon slash slash-en.wikipedia [dot]org/wiki/Image_segmentation #Level_set_methods)

Deformable models are popular methods for medical image segmentation and are widely used in curve evolution applications. They supply a continuous boundary of an object and are able to handle shape variations, image noise, heterogeneity, and discontinuous object boundaries. These challenging characteristics are very common in medical images. Level set models follow a non-parametric deformable model, thus are better at handling topological changes during evolution, compared to snake models. According to the mentioned above, level set can supply appropriate lesion segmentation in medical images. They can be classified into edge-based and region-based models. Edge-based models do not have a constraint of homogeneous image intensities, but are not ideal for noisy images, objects with incomplete boundaries, or for objects with low object-background contrast.

Edge-based models are not ideal for noisy images, objects with incomplete boundaries, or objects with low object-to-background contrast. Region-based models estimate spatial statistics of image regions to find the minimal energy where the model best fits the image. Chan and Vese [1] applied a region-based segmentation model with global constraint, based on the Mumford and Shah functional. The main advantage of the global constraint is its high robustness to the location of the initial contour [1,2]. However, in many cases such as with heterogeneous intensity areas, a local framework performs better than a global one [3-9]. Hybrid models are superior, defining an energy functional with local and global constraints to obtain a more accurate segmentation that is more robust to contour initialization [10]. Those methods allow curve deformation to find only significant local minima and delineate object borders despite noise, poor edge information, and heterogeneous intensity profiles [11]. Robustness to initial conditions is also an important measure of segmentation performance. Initial shape and position parameters (size, rotation, and location) need to be adequately determined; otherwise the contour may converge into a local minimum and may fail to capture the features of interest. The most common techniques for contour initialization are 1) manual selection of initial points; 2) analyzing the external force field; 3) naive geometric models such as a circle in 2-D or sphere in 3-D; 4) learned shape priors, where a statistical shape model is estimated, then the automated procedure tries to find the segmentation that best fits the shape model. However, shape prior-based methods may be quite restrictive in applications involving highly variable shapes.

Though the accuracy of contour initialization is important, the size of the local window surrounding each contour point plays a key role in the segmentation performance. The window size defines how the local scale of the statistics evaluation, and thus must be selected appropriately, even when initialization of the active contour is relatively accurate. Furthermore, well-defined local window can compensate on low-quality initial contour. Most local segmentation methods use candidates for pre-defined window sizes as input. Each candidate window size is tested over an extensive sequence of images to ascertain the best window size and this fixed window size is used for the entire database of images. However, this window size will not be optimal for all images and new images with different spatial statistics may require additional experiments to find the best window size. Thus, choosing a fixed window size by trial and error is a time consuming process. Moreover, when the images contain substantial diversity of spatial characteristics, pre-defining a single window size may result in non-optimal segmentation performance for all images. For that reason, a varied window size that is defined adaptively according to spatial information has a greater chance of providing accurate segmentation.

Some methods apply multi-scale segmentation by examining several Gaussian scales. The most accurate segmentation was obtained by using the smallest scale while with larger scale, the segmentation was more robust to contour initialization. However, for multi-scale methods a pre-specified pyramid of discrete Gaussian scales should be supplied as input. This may lead to high dependence of the segmentation accuracy on the number and the values of the discrete scales.

Recently, some works present a method to select the best scale from a range of input scales. However, choice of a single scale has some drawbacks. First, it may be sensitive to the criterion for choosing the best scale. Second, the scale choice is done by examining a specific scale each time, thus it depends on the local window only. However, in many images, global spatial characteristics can also contribute to the segmentation performance, and thus they need to be considered. Finally, these methods use the same size of the Gaussian kernel for both X and Y dimensions to define the local window (region), which may not be the best solution in cases for which image textures along the X and Y dimensions are different.

An et al. [12] implement a local framework at two different scales, which allows high sensitivity to different features. The authors show that the segmentation performance is better when using more than one single scale. Li et al. studied in depth the selection of kernel functions and its effect on the segmentation performance [5]. The authors applied their method using 3 different predefined Gaussian scales. As was expected, the most accurate segmentation was obtained by using the smallest scale while with larger scale was more robust to initialization. Yang and Boukerroui present a Gaussian scale selection based on the Intersection of Confidence Intervals rule [13]. The local scale is estimated, in the sense of minimizing the mean square error of a Local Polynomials Approximation (LPA). Pivano and Papadopoulo also applied a given pyramid of Gaussian kernels to compute local means and variances [14]. The chosen scale is the smallest one inducing an evolution speed superior to a threshold that is given by the user.

An inappropriate choice of level set parameters may lead to an inferior segmentation regardless of initialization. We propose a significant improvement of the level set segmentation method. We present an adaptive method to estimate the parameters for the level set energy function separately for each case and over iterations. When combined with estimation of an adaptive window size surrounding each contour point as suggested before, we supply a generalization of the segmentation process, applying the same model equations and deep learning architecture for any given dataset. Our method is a multi-stage process. First, we provide a novel method to estimate the parameters of the energy functional. A convolutional neural network (CNN) is used to identify the location of the zero level set contour in relation to the lesion. The output probabilities of the CNN are then used to calculate the level set parameters. Second, the adaptive window size is re-estimated by an iterative process that considers the scale of the lesion, local and global texture statistics, and minimization of the cost function over iterations. Our method requires only a single input point representing the approximate center of the detected lesion. There is no need of a more accurate initial contour as is typically supplied, automatically or manually, for local analysis. Contrary to current local active contour frameworks, our method has little to no dependence on accurate initialization and does not include any assumptions about lesion characteristics. Thus, it may perform well with highly diverse datasets that include low contrast, noisy, and heterogeneous lesions.

Few works provide an algorithm to estimate parameters for the level set energy functional. Li et al. [15] propose a fuzzy level set algorithm in which the level set parameters are initialized using a spatial fuzzy clustering approach. However, the parameters are only evaluated at the beginning of the segmentation process and remain constant throughout the whole process. In addition, the performance quality of fuzzy C-means is sensitive to noise, resulting in generally poorer segmentation. Oliviera et al. [16] present a solution for liver segmentation based on a deformable model, in which parameters are adjusted via a genetic algorithm. The genetic algorithm was used to choose the best combination of parameters from analysis of the training set, but all segmentations in the test dataset were conducted using the same parameters. Thus, this method may not be appropriate for highly diverse types of lesions. The authors in [16] also made two assumptions in their analysis: 1) the initialization is reasonably accurate; and 2) the liver is spatially homogeneous. Moreover, the authors use their method to segment the liver itself rather than a lesion dataset. The diversity of screened organs is typically much lower than the diversity that characterizes lesions. Baillard et al. [17] define the problem of parameter tuning as a classification of each point along the contour. That is, if a point belongs to the object, then the surface should locally extend, and if not, the surface should locally contract.

This classification is performed by maximizing the posterior segmentation probability [17]. However, the authors only consider the direction of the curve evolution and not its magnitude, which is critical especially in heterogeneous regions, wherein convergence into local minima should be prevented. Thus, both [16] and [17] are likely to have limited performance for highly diverse datasets, given the limited amount of information that is incorporated. We evaluated our proposed adaptive framework with two different energy models: the piecewise constant model and the mean separation model. Details of each model follow.

A. Piecewise Constant Model (PC)

Piecewise constant models are region-based models that assume intensity homogeneity. Chan and Vese [1] present a global framework of this PC model, which assumes intensity homogeneity. Let $F_{PC}(M_u, M_v, \phi)$ be a function which models the object and its background as uniform intensities represented by their means $M_u$ and $M_v$:

$$F_{PC}(M_u, M_v, \phi) = \mu \int_\Omega \delta\phi(x, y)|\nabla \phi(x, y)|dxdy + \lambda_1 \int_\Omega |I(x, y) - M_u|^2 H\phi(x, y)dxdy + \lambda_2 \int_\Omega |I(x, y) - M_v|^2 1 - H\phi(x, y)dxdy \qquad (1)$$

where $\mu$ affects the smoothness of the curve, and (x,y) is an examined location within a given image I. $\Omega$ is a bounded subset in $R^2$ and $\phi(x,y)$ is a signed distance map. $\nabla$ is the first variation of the energy with respect to the distance map $\phi(x,y)$. Let C be a parameterized curve, closed contour in $\Omega$ represented by the zero level set (ZLS). C={(x,y)|$\phi$(x,y)=0}. The interior region of C is defined by the smoothed Heaviside function H$\phi$(x,y).

$$H\phi(x, y) = \begin{cases} 1, & \phi(x, y) > \varepsilon \\ 0, & \phi(x, y) < -\varepsilon \\ \frac{1}{2}\left\{1 + \frac{\phi(x, y)}{\varepsilon} + \frac{1}{\pi}\sin\left(\frac{\pi\phi(x, y)}{\varepsilon}\right)\right\} & |\phi(x, y)| < \varepsilon \end{cases} \quad (2)$$

The external region of C is defined by (1-H$\phi$(x,y)). Representation of the narrow band around the ZLS contour C can be done by using the derivative of H$\phi$(x,y) and obtaining a smooth approximate version of Dirac delta $\delta\phi$(x,y).

By applying a local version of the PC model, M$_u$ and M$_v$ can be replaced by their local equivalent terms, m$_u$ and m$_v$. In that case, they will represent the local means of a region surrounding each contour point [3].

B. Mean Separation (MS) Model

The Mean Separation model was first proposed by Yezzi et al. [2]. It assumes that object and its background should have maximally separate mean intensities:

$$F_{MS}(m_u, m_v, \phi) = \qquad (3)$$

$$\mu \int_{\Omega_n} \delta\phi(x, y)|\nabla\phi(x, y)|dxdy + \lambda_1 \int_{\Omega_n} \left|\frac{I(x, y) - m_u}{A_u}\right|^2 H\phi(x, y)dxdy +$$

$$\lambda_2 \int_{\Omega_n} \left|\frac{I(x, y) - m_v}{A_v}\right|^2 (1 - H\phi(x, y))dxdy$$

$\Omega_n \in R^2$ is the local version of $\Omega$ which represents the narrow-band points, each point with its local surrounding only. A$_u$ and A$_v$ are the areas of the local interior and exterior regions surrounding a contour point, respectively:

$$A_u = \int_{\Omega_n} H\phi(x, y)dxdy, \; A_v = \int_{\Omega_n} (1 - H\phi(x, y))dxdy \qquad (4)$$

When m$_u$ and m$_v$ are the most different from each other, a minimization of the MS energy can be obtained. In some cases, the MS model may able to supply better results than the PC model due to preference of maximal contrast between the interior and the exterior regions without any restrictions on regions homogeneity. This allows to find image edges very well without considering if the interior or exterior regions are uniform or not.

C. Histogram Separation (HS) Model

Consider P$_u$(b) and P$_v$(b) to be two intensity histograms computed from the local regions, interior and exterior respectively, surrounding each ZLS contour point. N is the number of histogram bins. The Bhattacharyya coefficient B is chosen to evaluate the similarity of the two histograms [18]:

$$B = \int_{b=1}^{N} \sqrt{P_u(b)P_v(b)}\, db \qquad (5)$$

By separating the intensity histograms, the interior and exterior regions are allowed to be heterogeneous as long as their whole intensity profiles are different. By using the Bhattacharyya metric to quantify the separation of intensity histograms, we are able to segment objects that have local non-uniform intensities. There is no preliminary assumption regarding the gray level distribution of the object. However, the intensity profile of the entire object and the entire background must still be separable.

$$F_{HS}(x, y, \phi) = \qquad (6)$$

$$\int_{\Omega_n} B\left(\frac{1}{A_u} - \frac{1}{A_v}\right)dxdy + \lambda_1 \int_{\Omega_n} \left(\frac{1}{A_u} \times \sqrt{\frac{P_u(x, y)}{P_v(x, y)}}\, H\phi(x, y)\right)dxdy -$$

$$\lambda_2 \int_{\Omega_n} \left(\frac{1}{A_v} \times \sqrt{\frac{P_v(x, y)}{P_u(x, y)}}\, (1 - H\phi(x, y))\right)dxdy$$

Specific Patents and Publications

Guissin et al., "Inspection of region of interest," U.S. Pat. No. 9,082,165, issued Jul. 14, 2015, discloses a system that includes a data processing and analyzing utility responsive to input data indicative of one or more images of a region of interest and identifying one or more objects therein. The data processing and analyzing utility includes a visualization processor utility and a computer aided detection processor connected to the visualization processor utility. The computer aided detection processor is configured and operable for scoring said components according to one or more predetermined scoring schemes, and classifying the blobs and contours according to a degree of match with reference data indicative of one or more predetermined objects.

Gossett et al., "Method and apparatus for digital image segmentation using an iterative method," U.S. Pat. No. 6,803,920, issued Oct. 12, 2004, describes a method in which a digital image is divided into segments, wherein the digital image comprises an array of pixels each having a pixel location and a pixel color value. As explained there, image segmentation is the process of partitioning an image into a set of non-overlapping parts, or segments, that together constitute the entire image. Traditional edge-based segmentation uses differences in color or greyscale intensities to determine edge pixels that delineate various regions within an image. This approach typically assumes that when edge pixels are identified, the edge pixels will completely enclose distinct regions within the image, thereby indicating the segments.

Gerard et al., "Image processing method and system involving contour detection steps," U.S. Pat. No. 6,366,684, issued Apr. 2, 2002, discloses that it is known to model the problem of contour recovery as an energy minimization process. An energy function is associated with every candidate contour. These active contours are controlled by internal and external forces. The internal forces set the overall shape characteristics such as smoothness whereas external forces attract the contour towards local image features such as a high gradient value. The minimization is carried out by a discrete dynamic programming (DP) procedure. This technique is referred to as active contour (AC) detection. The method is iterative.

Puri, "Training convolutional neural networks on graphics processing units," U.S. Pat. No. 7,747,070, issued Jun. 29, 2010, discloses a convolutional neural network is implemented on a graphics processing unit. The network is then trained through a series of forward and backward passes, with convolutional kernels and bias matrices modified on each backward pass according to a gradient of an error function.

SUMMARY

The following brief summary is not intended to include all features and aspects of the present invention, nor does it imply that the invention must include all features and aspects discussed in this summary.

In certain aspects, provided are computer-implemented methods for characterizing a feature of interest in a digital image, using an adaptive local window. In some embodiments, the methods include obtaining an initial contour for a feature of interest (e.g., 1-point radiologists manual markings on an image), the initial contour formed of contour points; defining a region of interest around said contour; and segmenting the feature of interest by iteratively selecting a size of a local window surrounding each point on said contour, where the local window size is determined based on (i) homogeneity, (ii) contrast surrounding each contour point, (iii) approximate lesion size, and (iv) an energy function, wherein the energy decreases as the segmenting progresses.

As used herein, the term "region of interest" refers to a figure created on the image surrounding the contour; the adaptive local window is created by considering the factors described here.

In some embodiments, the initial contour is represented as an initial zero level set. In certain aspects, selecting a size of a local window includes calculating spatial statistics only for pixels that are within a narrow range 10 pixels of the zero set level. In some embodiments, the region of interest has a shape selected from the group consisting of: a square, a rectangle, a circle, and an oval. In certain aspects, homogeneity is calculated by determining Haralick texture features. In some embodiments, the energy function includes a calculation of a mean-curvature flow-like evolving the active contour. In certain aspects, a smaller local window is used when contrast in the digital image is low, a larger local window is used when the digital image contains a high level of noise or heterogeneity, or both. In some embodiments, the segmenting stops automatically at a set degree of convergence between iterations. In certain aspects, the segmenting step is automated. In some embodiments, the defining and segmenting steps are automated. In certain aspects, the obtaining, defining, and segmenting steps are automated.

According to certain embodiments, provided are computer-implemented methods for characterizing a feature of interest in a digital image, using a calculated adaptive level set method. Such methods include obtaining an initial contour for a feature of interest; and producing an evolved contour towards the boundary of the feature of interest, wherein the producing includes determining weighting parameters of a level set function using a convolutional neural network (CNN). The weighting parameters are determined based on output probabilities from the CNN that are probabilities of the initial contour being inside the feature of interest and far from its boundaries, outside the feature of interest and includes it and far from its boundaries, or close to a boundary of the feature of interest. The weighting parameters control the direction and magnitude of contour evolution.

In certain aspects, the weighting parameters are calculated using a formula considering probabilities of: inside the feature of interest and far from its boundaries (p1); outside the feature of interest and includes it and far from its boundaries (p3); close to a boundary of the feature of interest (p2), where if p3>p1 the contour shrinks, if p1>p3, the contour expands, and p2 acts as a stabilizing factor.

In certain aspects, "far" means the distance between the contour and the feature of interest is the same or greater than half of the radius of an equivalent reconstructed circle of the feature of interest, and "close" means the distance between the contour and the feature of interest is less than half of the radius of an equivalent reconstructed circle of the feature of interest.

In some embodiments, the CNN includes two convolutional blocks, followed by two dense layers, including a final three-node layer. In certain aspects, the CNN uses raw images as feature maps. In some embodiments, the CNN includes a filter bank layer that convolves each input feature map with a set of learned weights/filters. In certain aspects, the CNN includes a non-linear activation applied to the output of the filter layer to obtain features that are non-linear transformations of the input. In some embodiments, the convolutional neural network includes methods to prevent over-fitting, dropout and channel-wise normalization.

In certain aspects, methods are provided that combine the methods as described above, using an adaptive local window, with the methods described above including determining weighting parameters of a level set function using a convolutional neural network (CNN), whereby further characterization of the feature of interest is achieved.

In any of the methods of the present disclosure, a feature of interest may be a lesion. In some embodiments, the feature of interest is a lesion in a digital medical image. Digital medical images of interest include, but are not limited to, a magnetic resonance imaging (MRI) image, a computed tomography (CT) image, a mammogram, and an X-ray image.

Also provided are non-transitory computer readable medium comprising instructions for causing a system to perform one or more steps of any of the methods of the present disclosure.

In certain aspects, provided are systems that include a processor and a non-transitory computer readable medium including instructions for causing a system to perform one or more steps of any of the methods of the present disclosure.

BRIEF DESCRIPTION OF THE DRAWINGS

FIG. 15A through 15C is a set of images showing lesion segmentation using the proposed method.

DETAILED DESCRIPTION

Overview

Figures 1A, 1B:
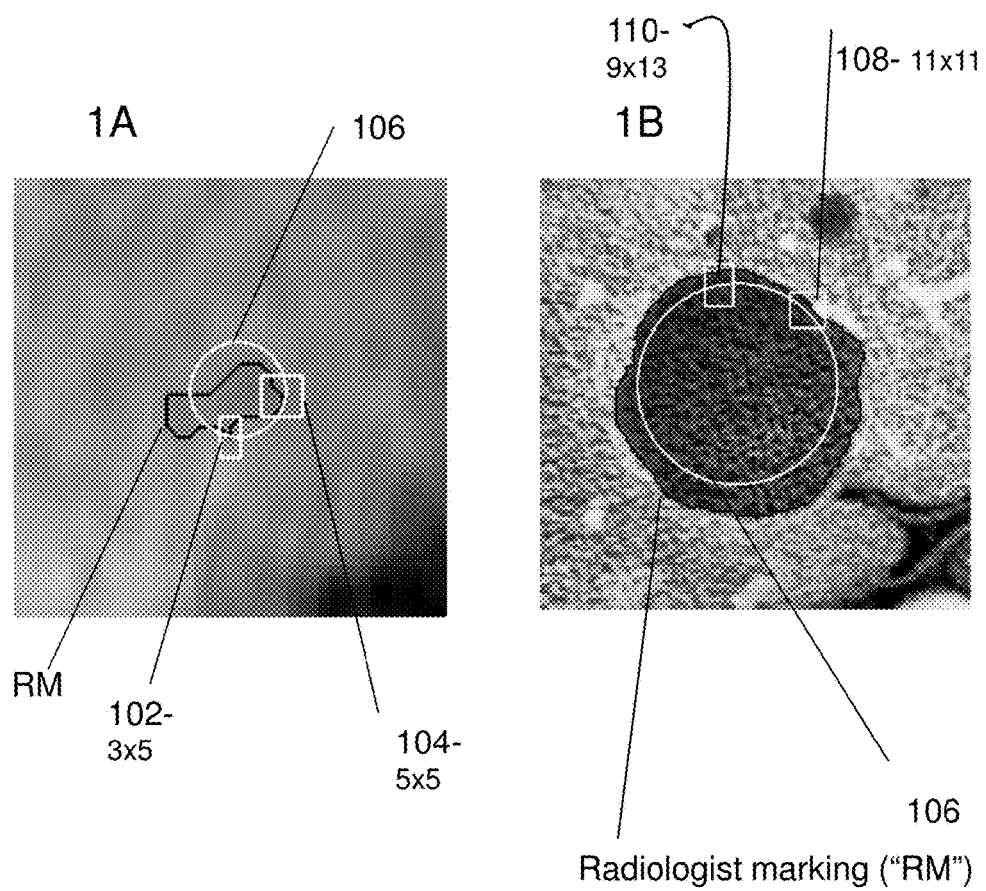
FIGS. 1A, 1B is a pair of images demonstrating different window sizes that were evaluated for different lesions and for different contour points.

The present invention comprises a method for determining a local window surrounding each contour point. Further, the invention comprises an improved method of selecting parameters that are used for the segmentation.

Defining Local Window and Parameters of the Energy Functional

An appropriate local window surrounding each contour point can improve the segmentation quality a lot. However, choice of inappropriate parameters of the energy functional may lead to an inferior segmentation, even if the contour initialization or the chosen local window is sufficient for segmentation. In addition, the user does not usually have the experience to tune the parameters or the local window appropriately. Therefore an adaptive solution is desired for clinical applications of image processing Level Set Segmentation Local frameworks of level set segmentation usually utilize a fixed size local window surrounding each contour point and fixed parameters of the energy functional ($\lambda_1$, $\lambda_2$). These level set parameters (window and energy parameters) are usually chosen experimentally and cannot be changed during the segmentation process. Therefore, the segmentation performance is highly dependent on the accuracy of the contour initialization and on the texture complexity of the object that should be segmented. Disclosed herein is a method to specifically improve the level set segmentation. In particular, we present two relevant contributions. First, we provide a semi-automated method to determine the local window size surrounding each contour point. The window size is evaluated by utilizing 1) the object scale, 2) the local and global texture statistics, and 3) the minimization of the cost function. The rationale for choosing those criteria is the substantial diversity of these lesions characteristics. Those considerations are reflected in the present method. This pixel-wise method re-evaluates iteratively the local window size, separately for X and Y window dimensions. The adaptive process is applied for each contour point, over iterations and for different lesions in the image database. It allows higher sensitivity to texture changes that appear along the contour and during its evolution.

Second, we provide a semi-automated multi-step method to estimate the parameters of the energy functional. These parameters are defined by using Convolutional Neural Network (CNN) to detect the location of a Zero Level Set (ZLS) contour in relative to the lesion. The CNN outputs the probabilities that the ZLS contour is located being (i) inside the region of interest and far from its boundaries, (ii) outside the region of interest and includes it and far from its boundaries or (iii) close to a boundary of the region of interest. Then, $\lambda_1$, $\lambda_2$ are evaluated by using the output classification probabilities. As a result, one not only obtains the direction of the contour evolution, but also its magnitude that is important to prevent convergence into local minima in heterogeneous regions, or "leakage" of the contour in case of low contrast lesions. The parameters are evaluated for every lesion separately and over iterations by utilizing texture analysis and deep learning architecture.

The method requires only the detection of the lesion as an input. It has no need of more accurate initial contour as should be usually supplied for local analysis. Therefore, the method can adapt itself better to texture diversity. It has no dependence on accurate initialization. Moreover, it does not include any preliminary assumptions on the lesion characteristics, thus it may perform well with low contrast lesions as well with noisy or heterogeneous lesions.

The method was also evaluated by using different contour initializations. Those contour have been initialized by using different diameters and by placing them at different locations in relative to the lesion center. The presented method performs better than the fixed parameters level set method and was affected less by different initializations. The presented method utilizes both local and global statistics, thus on one hand, it supplies more accurate segmentations, and on the other hand, it provides higher robustness to changes of the location of the initial contour. The method shows significantly better agreement with human observers than state of the art methods. It outperforms for all tested configurations, including different local energies and contour initializations, and for different levels of lesion complexity.

Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, digital image analysis are those well-known and commonly used in the art. Certain computer techniques, not specifically defined, are generally performed according to conventional methods well known in the art and as described in various general and more specific references that are cited and discussed throughout the present specification. For purposes of clarity, the following terms are defined below.

Ranges: For conciseness, any range set forth is intended to include any sub-range within the stated range, unless otherwise stated. As a non-limiting example, a range of 120 to 250 is intended to include a range of 120-121, 120-130, 200-225, 121-250 etc. The term "about" has its ordinary meaning of approximately and may be determined in context by experimental variability. In case of doubt, the term "about" means plus or minus 5% of a stated numerical value. Similarly, a stated range, for example, of 90 to 95 present should be read as a possible range of 91-92, 90-92, 90-93, etc.

The term "level set model" refers to a tool for numerical analysis of surfaces and shapes. The model is an energy functional that contains internal and external terms that are applied to evolve the segmentation contour.

The term "local window" refers to a region surrounding each contour point.

The term "boundary" refers to an edge delineating a feature of interest in a digital image.

The term "contour" and "contour points" refers to the curve (and the discrete points that are placed on it) that is used to delineate the desired feature.

The term "active contour" refers to a contour that is modified by a calculation that allows a contour to more closely approach an image boundary, as described, e.g. in Gerard et al., above.

The term "evolving a contour" refers to the progress of a segmentation process by moving the contour towards the desired feature to be segmented.

The term "energy function" refers to a mathematical equation (i.e. functional) used in level set applications. Minimization of this functional will result delineation of the feature. The present method applies 3 different energy functions—PC, MS and HS, as described below.

The term "homogeneity" refers to level of similarity between grey values of neighbor pixels.

The term "Haralick texture features" refers to type of spatial characteristics such as homogeneity or contrast.

The term "contrast" refers to the grey level difference between neighbor pixels.

The term "extracting probabilities" refers to Convolutional Neural Network (CNN) output. The network will supply 3 different values—the chances that a contour is inside the desired object, near its boundaries or outside it.

The term "convolutional neural network" refers to type of machine learning technique that uses a bank of existing and analyzed data in order to classify new data. A convolutional neural network as described below will include convolutional blocks, followed by two dense layers, including the final three-node layer, which can be termed a set of learned weights/filters.

The term "filter bank" refers to a group of matrices that are used to convolve local windows inside an image, to get a new image.

The term "over-fitting" refers to a result that occurs when a statistical model describes random error or noise instead of the underlying relationship. Over-fitting generally occurs when a model is excessively complex, such as having too many parameters relative to the number of observations.

The term "raw image" refers to the original image before any additional processing has been applied on it.

General Methods

As was mentioned above, in this work we present an adaptive local level set method, which evaluate adaptively the local window surrounding each contour point and the parameters of the energy functional.

Adaptive Local Window

Figure 4:
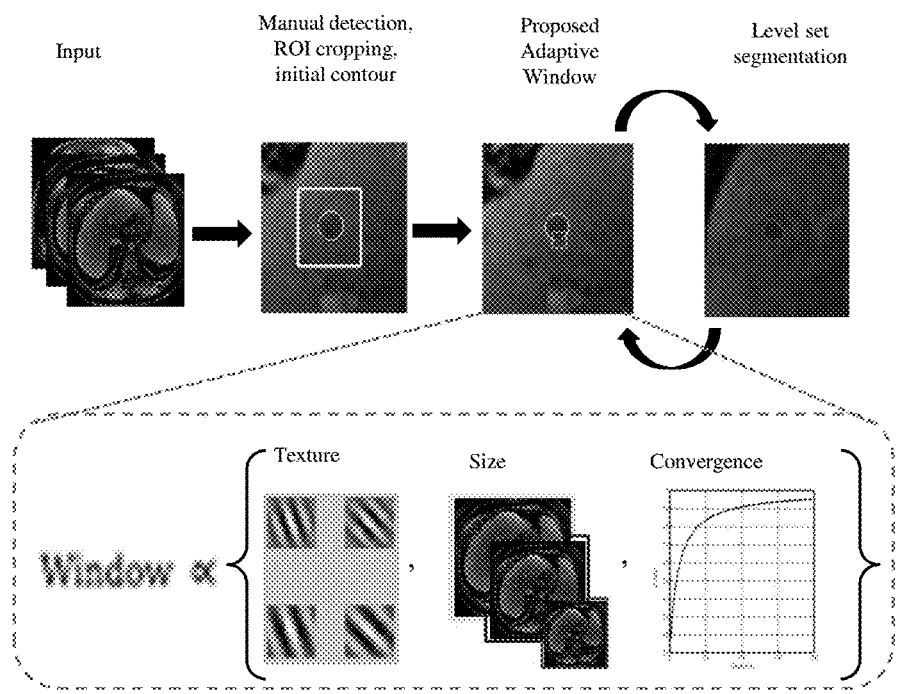
FIG. 4 is a schematic diagram showing steps for calculating the optimal window size for each contour point. The upper scheme presents the overall steps of a method according to one embodiment. The lower scheme focuses specifically on the calculation of the local adaptive window.

Local version of the described energies requires a definition of a local window, in which the energy cost function is calculated. In the present method, we evaluate adaptively the size of the local window. By using different window sizes for different lesions and contour points, the segmentation should fit better to any change in the spatial statistics. The process for determining the adaptive window is illustrated in FIG. 4.

To accommodate varying spatial characteristics in the X and in the Y dimensions, the window dimensions are calculated for each axis separately by considering the approximate lesion size, the convergence of the energy functional and the respective texture components only. FIGS. 1A and 1B demonstrate the use of different window sizes that were estimated for different lesions and for different contour points. Different sizes of window X, Y dimensions are illustrated in pixels.

FIG. 1A shows a low contrast MRI liver lesion. Rectangular window 102—2.4 mm×4 mm pixels, square window 104—4 mm×4 mm. FIG. 1B shows a noisy CT liver lesion. Square window 108—8 mm×8 mm, rectangular window—7 mm×9 mm. Black irregular contour—radiologist manual marking. White contour 106—initial zero level set (ZLS) contour. To accommodate varying spatial characteristics in the X and in the Y dimensions, the window dimensions are calculated for each axis separately by considering the respective texture components only.

We proposed an iterative approach to calculate the adaptive size of the local window. The algorithm is applied for each point at each iteration and for each lesion in the image database. The adaptive window is applied separately for the X and Y window dimensions and is calculated using the lesion scale and its texture. Let $L_x$, $L_y$ be the approximate x and y lesion dimensions defined by a generated bounding box surrounding the lesion. Since we minimize user input by requiring only a single input point, we approximate lesion size by generating a surrounding bounding box. In $\theta \in \{0, 90, 180, 270\}$ addition to the lesion size, successfully dealing with high lesion diversity requires considering spatial image texture. Texture analysis is accomplished by extracting Haralick image features (e.g. contrast, homogeneity) from a second order statistics model, namely, gray-level co-occurrence matrices (GLCM) [20]. Our method incorporates both global and local texture in a single hybrid model. For each point (x, y) examined in image I, we compare pairs of pixels, where the second pixel in the pair is $(x+\cos\theta, y+\sin\theta)$, located at $\theta \in \{0, 90, 180, 270\}$ degrees relative to the first pixel. Let W be a local window of $X_w \times Y_w$ pixels, surrounding an examined contour point within a region I. The co-occurrence matrix $P(m, n, \theta)$ of W is defined as the number of pixel pairs (x, y) and $(x+\cos\theta, y+\sin\theta)$ in W with grey values of (m,n):

$$P(m, n, \theta) = \sum_{x=1}^{X_W} \sum_{y=1}^{Y_W} \begin{cases} 1, & I(x, y) = m \text{ and } I(x + \cos\theta, y + \sin\theta) = n \\ 0, & \text{otherwise} \end{cases} \quad (11)$$

Then, homogeneity and contrast criteria are evaluated for each $\theta$ as:

$$\text{Homogeneity}(\theta) = \sum_{m,n=0}^{N_G-1} P(m, n, \theta)(1 + |m - n|^{-1}) \quad (12)$$

-continued $$\text{Contrast}(\theta) = \sum_{m,n=0}^{N_G-1} P(m, n, \theta)(|m-n|^2),$$

where $N_G$ is the total number of grey levels. These spatial criteria are averaged for each individual axis, X and Yθs. For local analysis, criteria are evaluated for each ZLS point separately while for global analysis, those criteria are calculated and averaged over all points within the lesion's bounding box. According to eq. (12), we define GH as the global homogeneity, GC as the global contrast and $LC_{x_{ij}}$, $LC_{y_{ij}}$ as the local contrast in the x and y directions surrounding the $i_{th}$ contour point at the $j_{th}$ iteration. The interaction between the global and the local terms plays an important role in determining the window size. For each $i_{th}$ contour point, the local contrasts $LC_{x_{ij}}$, $LC_{y_{ij}}$ are re-estimated at each $j_{th}$ iteration. On the other hand, the method computes the global contrast, GC, and the global homogeneity, GH, only once within the entire region of interest (ROI). The adaptive window size is then calculated as:

$$\hat{W}_{x_{ij}} = \frac{L_x}{\log(L_x)} \times \frac{1}{\left(GH + \frac{1}{GC} + \frac{1}{LC_{x_{ij}}} + \frac{1}{\bar{F}_{j-1}}\right)} \quad (13)$$

$$\hat{W}_{y_{ij}} = \frac{L_y}{\log(L_y)} \times \frac{1}{\left(GH + \frac{1}{GC} + \frac{1}{LC_{y_{ij}}} + \frac{1}{\bar{F}_{j-1}}\right)},$$

where $\bar{F}_{j-1}$ represents the average value of the energy functional over all ZLS contour points during the previous iteration. As long as curve evolution continues, the average value of $\bar{F}_{j-1}$ should decrease as the size of the local window decreases.

Energy Functional Parameters

Figure 5:
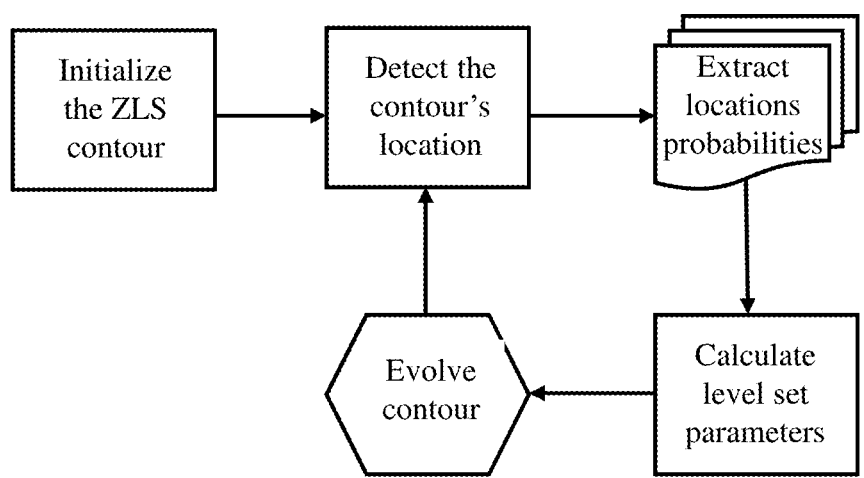
FIG. 5 is a schematic diagram showing a method according to one embodiment for learning level set parameters.

Level set curve evolution depends on three weighting parameters. μ controls the smoothness of the contour and is fixed at μ=0.1 throughout the segmentation process. The level set framework is relatively insensitive to changes in the value of μ. On the other hand, λ1 and λ2 play a key role in the direction and magnitude of curve evolution. Curve evolution depends not only on the absolute values of these parameters, but also on their ratio. The proposed method involves a two-step, iterative process that supplies an Adaptive estimation of the active Contour Parameters via machine learning-based evaluation. First, a convolutional neural network (CNN) is used to estimate the location of the ZLS contour relative to the lesion [21]. Three possible locations are considered: outside, near, or inside the lesion boundary. The process for determining the level set parameters is illustrated in FIG. 5.

Given a contour, the convolutional neural network outputs probabilities for each of the three classes: inside the lesion and far from its boundaries ($p_1$), close to the boundary of the lesion ($p_2$), and outside the lesion, includes it and far from its boundaries ($p_3$). Sum of these probabilities equals 1. $\lambda_1$, $\lambda_2$ are calculated by using the following equations:

$$\lambda_1 = e^{\frac{1+p_2+p_3}{1+p_1+p_2}}, \lambda_2 = e^{\frac{1+p_1+p_2}{1+p_2+p_3}} \quad (15)$$

If $p_3 > p_1$, then $\lambda_1 > \lambda_2$ and the contour has a tendency to contract. Conversely, if $p_1 > p_3$, then $\lambda_2 > \lambda_1$ and the contour tends to expand. Probability $p_2$ serves as a stabilizer and a restraining factor. That is, if the ZLS contour is located close to the lesion's boundaries, $p_2 \gg p_1$, $p_3$ and $\lambda_1 \approx \lambda_2$. As a result, both energies, related to the regions inside and outside the contour, are weighted equally. The exponential function is used to increase the range of values and ratios that $\lambda_1$ and $\lambda_2$ can take on.

CNN (Convolutional Neural Network) Architecture

Figure 6:
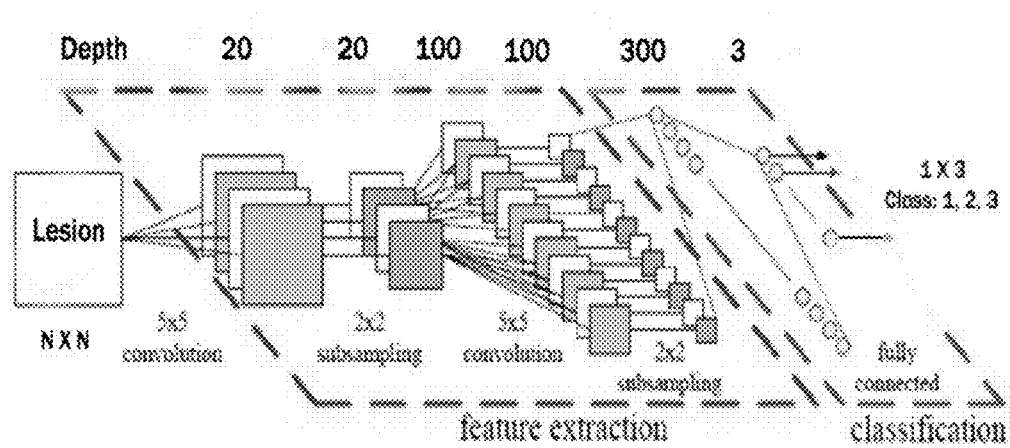
FIG. 6 is a schematic diagram showing CNN architecture according to one embodiment. The input is an N×N image of a lesion. Two convolutional blocks follow the input, with 5×5 filters and 2×2 max pooling.
Figure 7:
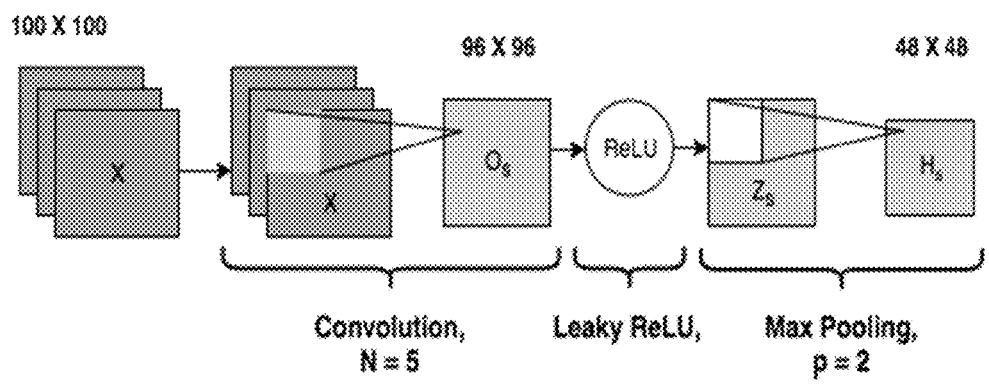
FIG. 7 is a schematic diagram showing a sample convolutional block with filter bank, leaky ReLU and max pooling. The example input is a stack of 100×100 images, which are then convolved by 5×5 filters to create feature maps of dimension 96×96. Following leaky ReLU activation, 2×2 max pooling reduces the dimension by a factor of 2.
Figure 8:
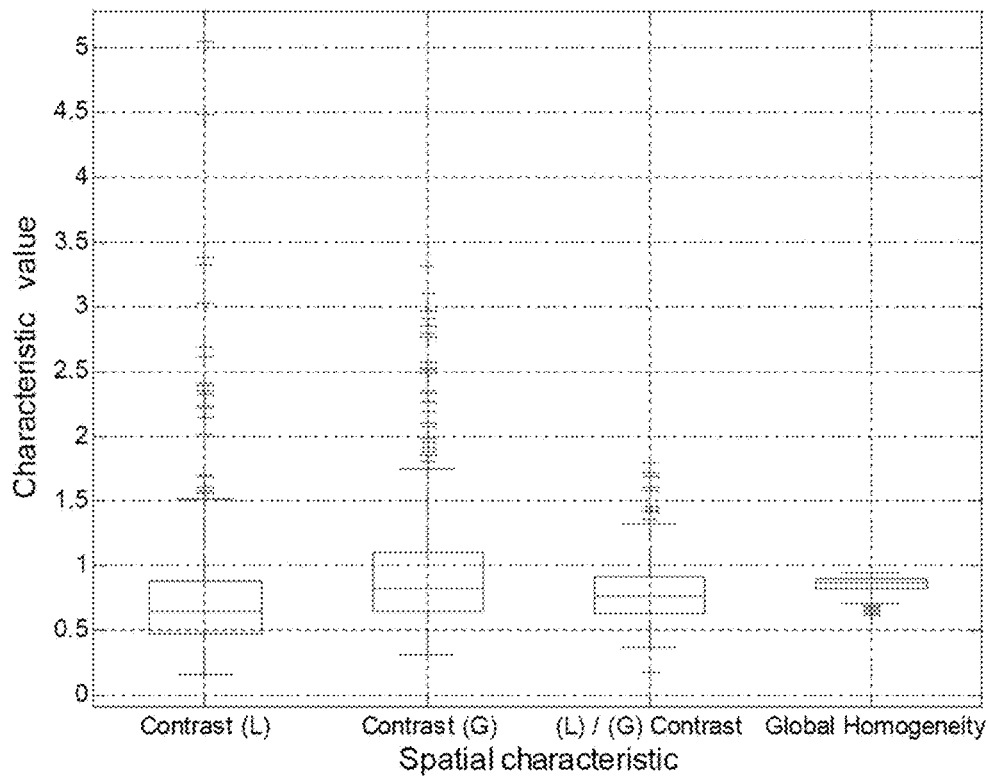
FIG. 8 is a graph showing the spatial characterization of the lesions (local) and the whole ROI (global). (L)—lesion. (G)—the global ROI.

Our architecture consists two convolutional blocks, followed by two dense layers including the final three-node layer. 5×5 pixels filters were used, due to their best performance (FIG. 6. FIG. 6 shows the CNN architecture, where the input is an N×N image of a lesion. Two convolutional blocks follow the input, with 5×5 filters and 2×2 max pooling. The present method uses the raw images as the feature maps. Each stage of the CNN is composed of three layers: a filter bank layer, a nonlinearity layer (Leaky ReLU "Rectified Linear Unit"), and a feature pooling layer (FIG. 7). FIG. 7 shows a sample convolutional block with leaky ReLU and max pooling. The example input is a stack of 100×100 images, which are then convolved by 5×5 filters to create feature maps of dimension 96×96. Following leaky ReLU activation, 2×2 max pooling reduces the dimension by a factor of 2. Convolutional neural networks often contain a series of these units.

Filter bank layer convolves each input feature map with a set of learned weights/filters. Each filter is a small 5*5 pixels region, but extends through the full depth of the input volume. The amount of learnable filters is restricted by the size of the image, but the depth of the output volume is a user-defined parameter that controls the amount of neurons that connect to the same region of input volume.

Non-Linear Activation is applied to the outputs of the filter layer to obtain features that non-linear transformations of the input [21]. The Rectified Linear Units (ReLU) use the following activation function that has recently become the gold standard for training deep neural networks due to its fast convergence:

$$f(x) = \max(0, x) \quad (16)$$

Glorot et al. [22] argued that the ReLU function's hard zero limit mimics the sparse activation of neurons in the brain. However, ReLU units are at a potential disadvantage because early zeroing can mean that a particular neuron will not activate for the remainder of training. Leaky ReLU units alleviate this problem by allowing a small, non-zero gradient if the unit is not active:

$$f(x) = \begin{cases} x, & x > 0 \\ 0.01x, & \text{else} \end{cases} \quad (17)$$

Leaky ReLU activation function reduced over-fitting and leads to lower error rates while training.

Max-pooling is the final step of the feature extraction of CNN. We use this technique to reduce the dimensionality of the dataset. Max-pooling takes a small sub-region from the Leaky ReLU output and represents it by its maximum value.

The CNN attempts to minimize the following cost function:

$$L(w) = \frac{1}{n}\sum_{i=1}^{n} \ell(z, f(x, w)) + \frac{\eta}{2}\|w\|^2, \quad (18)$$

for a labeled training set $(x_1, z_1), \ldots, (x_n, z_n)$ and weights $w = (w_1, \ldots, w_L)$, and some loss function l. L2-regularization penalizes the size of the weights in the model, where η=0.005 is the coefficient of regularization. Stochastic gradient descent with momentum is applied to update the weights ($w_i$) of the network [21]:

$$v_{i+1} = \zeta v_i - \alpha \nabla w_i - \eta w_i$$

$$w_{i+1} = w_i + v_{i+1} \quad (19)$$

where i is the iteration index, v is the previous gradient, ζ is the same regularization coefficient that appears in (18) and ζ is the momentum. The latter was initialized to 0.95 [21]. Momentum-based methods damp the gradient and provide better convergence rates for deep networks. Xavier initialization is used to initialize the weights in each layer from a normal distribution of N(0, $10^{-4}$) [21]. This initialization ensures that the signal remains within a reasonable range of values through the network. We use an equal learning rate, α, for all layers, which was adjusted via validation checks. The learning rate was initialized at 0.01 [21]. After each epoch, if the error of the validation set (80/20 split for training) remains the same or increases, then the learning rate is decreased by a factor of 2. The CNN is trained with mini-batch stochastic gradient descent with a batch size of 128 images. Log loss is used to evaluate the performance of the network after each batch:

$$f(z, f(x, w)) = -\frac{1}{N} \sum_{n=1}^{N} \sum_{m=1}^{M} B_{m,n} \log(p_{m,n}), \quad (20)$$

where N is the number of training examples in the batch, and M is the number of classes. When the $n_{th}$ example is classified into the $m_{th}$ class, $B_{m,n}$ equals 1. Otherwise, $B_{m,n}$ equals 0. $P_{m,n}$ is the probability of the $n_{th}$ example being classified into the $m_{th}$ class.

Over-Fitting

We used two methods to prevent over-fitting, dropout and channel-wise normalization. Dropout, introduced by Hinton et al. [23], randomly drops hidden nodes and connections from the network during time, thus preventing the hidden nodes from co-adapting with each other and improving the generalization of the network. Dropout has been shown to reduce over-fitting and significantly improve training and testing accuracy. We also used channel-wise normalization after every convolutional and fully-connected layer, which Krishevsky et al. found reduced their error rate. The function is defined as:

$$y_{i,j}^k = \frac{x_{i,j}^k}{\left(\kappa + \alpha \sum_{q \in N_k} (x_{i,j}^q)^2\right)^\beta} \quad (21)$$

Where $$q = \left[\max\left(0, k - \frac{n}{2}\right), \min\left(N - 1, k + \frac{n}{2}\right)\right].$$

The sum runs over n "adjacent" feature maps at the same spatial position. $\alpha = 10^{-4}$, $\beta = 0.75$, $\kappa = 2$ and $n = 5$ are hyperparameters that we set according to Krishevsky et al. This normalization is related to the lateral inhibition found in real neural networks.

IV. Implementation Details

Image Preprocessing

Normalization of the grey values is done for each image separately. We apply Contrast-Limited Adaptive Histogram Equalization (CLAHE) with a uniform distribution to enhance low contrast lesions, while preventing enhancement of noise. Due to the high diversity of our dataset, both low contrast and noisy regions exist. Then, bilinear interpolation is applied between neighboring patches to eliminate artificially induced boundaries.

Lesion Detection and Distance Map Reconstruction

Figure 2:
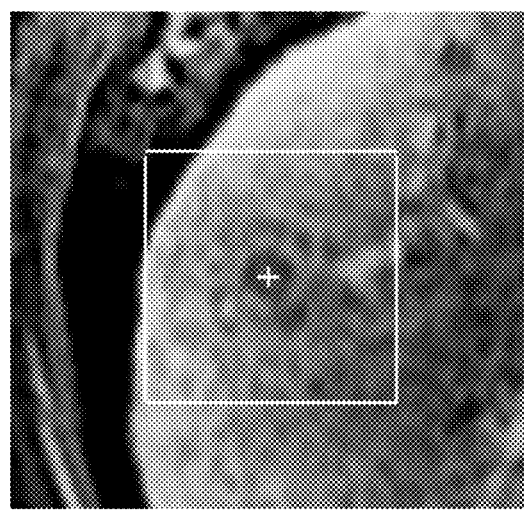
FIG. 2 is an image showing reconstruction of a region of interest (ROI). The white plus sign is an input point supplied by a radiologist.

Two Board-certified abdominal imaging radiologists manually detected all lesions and traced the liver lesions on each single 2D slice. They marked one point that approximate the lesion's center (white star, FIG. 2), from which a Region Of Interest (ROI) and an initial circular zero level set (ZLS) contour are obtained. The ROI (white rectangle) is constructed by taking a 10-pixels interval from those edge points. By using adaptive parameters of the energy functional, we are able to decide if a specific contour is inside or outside the lesion.

Narrow-Band

Figure 3:
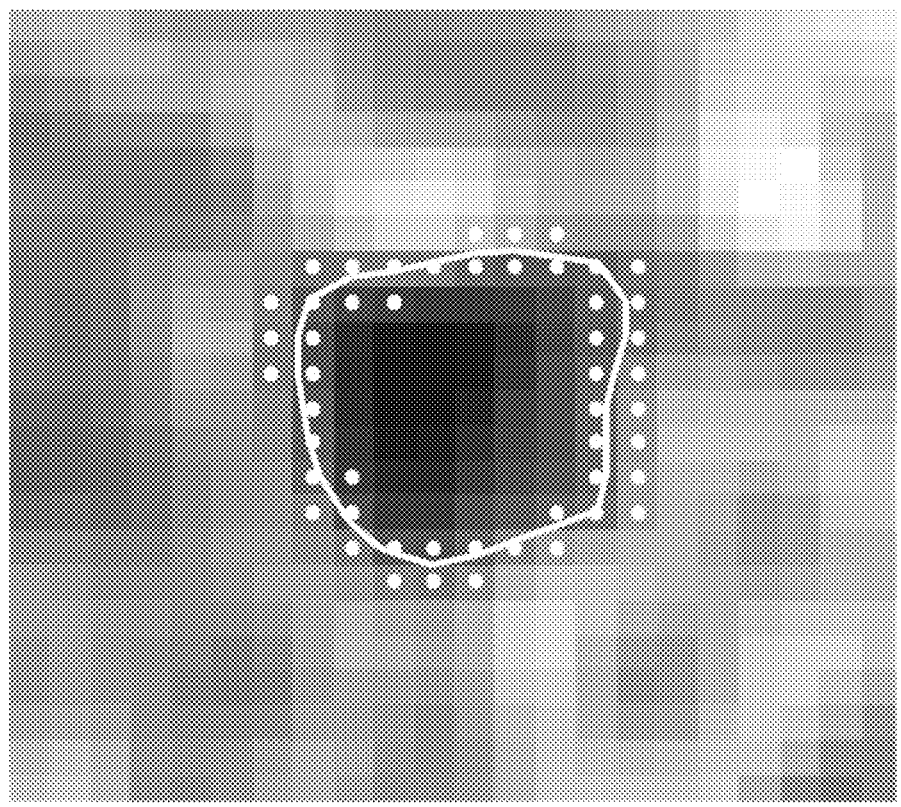
FIG. 3 is an image showing the zero level set contour with a chosen narrow band. The white contour represents a zero level set around a lesion. The white dots represent narrow band points.

The present method calculates the spatial statistics only for grid points that are located within a narrow-band of the distance map φ(x,y) around C (FIG. 3). Chopp was the first to introduce the narrow-band idea, which became very popular in implementations of local segmentation frameworks. The segmentation process begins with initialization of every pixel within the narrow band with values of exterior and interior statistics. An update of the distance map φ(x,y) occurs only within the narrow band. Therefore, while using the local framework, the initialization computations can be significantly reduced, depending on the size of the local window and on the initial location of the contour relative to its final position.

FIG. 3 shows a zero level set contour with a chosen narrow band. The white contour represents a zero level set around a lesion. The white dots represent narrow band points.

Data Augmentation

Convolutional neural networks, due to their size and complexity, typically require substantial datasets to perform optimally. Therefore, data augmentation was applied to the original images to artificially increase the size of the training set. Data augmentation was performed using a combination of elastic and affine distortions. These distortions are applied by generating random displacement fields with values in the range of [−1 1], convolving these fields with a Gaussian filter of standard deviation σ=[3 8] and multiplying the resulting matrices by a constant factor α with discrete values of [8, 12, 16, 24, 30, 36], which controlled the magnitude of the deformation. The σ and α parameters have been chosen based on visual inspection-values less than 8 didn't produce sufficient variation, while values higher than 36 distorted the images too much. After the image was non-rigidly distorted, one applies affine transformation to design a scaling-rotation-translation invariant method.

EXAMPLES

Data

This study was approved by the institutional review board of the present institution (IRB). It includes analysis of 276 liver lesions divided into 2 subsets. The first subset contains 112 contrast-enhanced CT images (Siemens Medical Solutions, Erlangen, Germany) of liver lesions (20 Hemangiomas, 25 Cysts and 24 Metastases) from patients scanned at a single academic institution. Cysts were non-enhancing water-attenuation circumscribed lesions. Hemangiomas showed typical features of discontinuous nodular peripheral enhancement, with fill-in on delayed images. Metastases were hypo-attenuating, had soft-tissue internal attenuation, enhanced homogeneously with contrast material administration, and had less well-defined margins than cysts. The following image acquisition parameters were used: 120 kVp, 140-400 mAs, 2.5 mm-5 mm section thickness and pixel spacing of 0.704 mm±0.085 mm.

The second subset includes 164 liver lesions from MRI scans with cirrhosis scanned at a different academic institution. All patients underwent 3T gadoxetic acid enhanced MRI (Signa Excite HDxt; GE Healthcare, Milwaukee, Wis.) at one tertiary liver center for evaluation of suspected hepatocellular carcinoma (HCC) and were found to have one or more LIRADS (LR)—LR-3 or LR-4 lesions. Such lesions are thought to have intermediate (LR-3) or high (LR-4) probability of being HCC. We focused in this study on LR-3 and LR-4 lesions because they tend to be diverse in their spatial texture and hence provide a challenge for automated segmentation. Slice thickness was 5 mm and pixel spacing of 0.805 mm±0.078 mm. Pulse sequences of Single-shot fast spin-echo T2-weighted and pre and post contrast Axial 3D T1-weighted fat-suppressed gradient-echo were used.

For the 276 lesions, a wide range of lesion sizes was found. The smallest MRI liver lesion was 16.87 mm×14.06 mm while the largest was 32.81 mm×36.56 mm. The size of CT liver lesions ranged between 18.58 mm×20.20 mm and 125.24 mm×132.15 mm. Additional spatial characteristics, such as homogeneity and contrast, of the lesions and the whole ROIs were present due to different imaging modalities and clinical diagnoses. There was great diversity of the lesion textures for ROI homogeneity (0.88±0.04), ROI contrast (0.76±0.25) and ROI size (14.24±4.38 pixels).

The spatial characteristics of all 276 lesions have been estimated (see graph in FIG. 7). High diversity of the lesion characteristics was found. It illustrates the importance and the need for an adaptive local window size that is able to handle such a wide range of spatial texture. These spatial criteria serve as key ideas for the present method.

The radiologists' manual markings have been used for the evaluation of the present method. The automated segmentation contours were extracted and quantitatively compared with the average radiologists' marking. In order to investigate the sensitivity to initialization (section on Sensitivity to Initialization, below), we changed the location of the approximate lesion center point that was supplied by the clinician.

Results

Figure 9A:
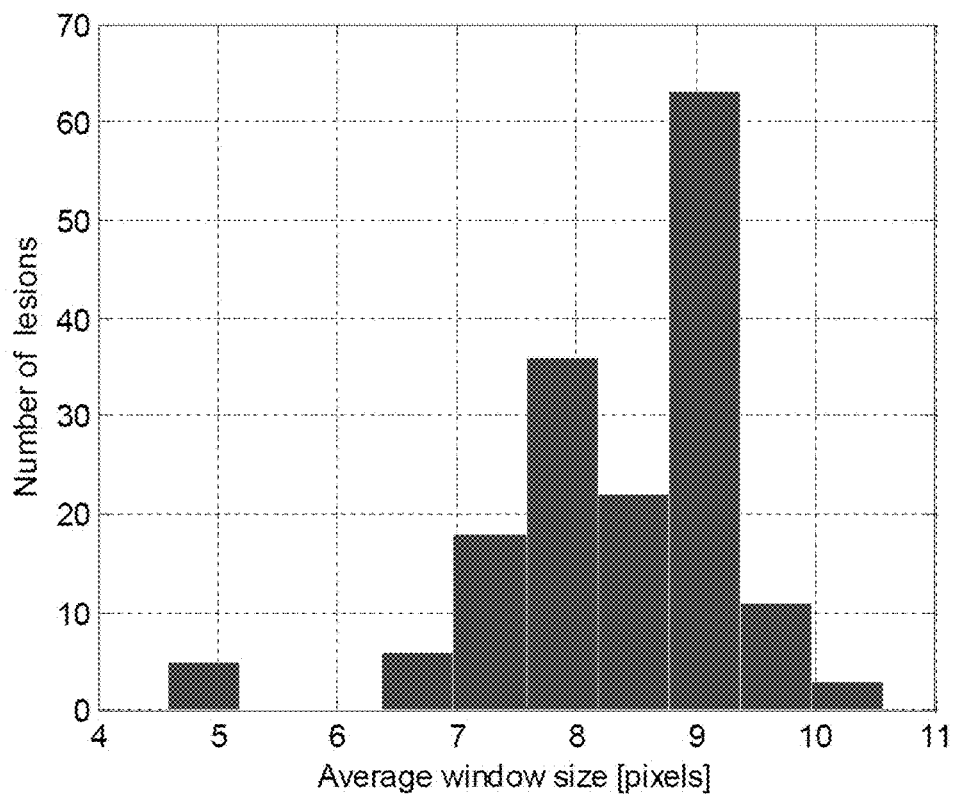
FIG. 9A, 9B is a pair of graphs showing the distribution of the local window sizes for MRI liver lesions (9A) and CT liver lesions (9B). For each lesion, the representative value is the average size of X and Y window dimensions, for all contour points over all iterations of the segmentation process.
Figure 9B:
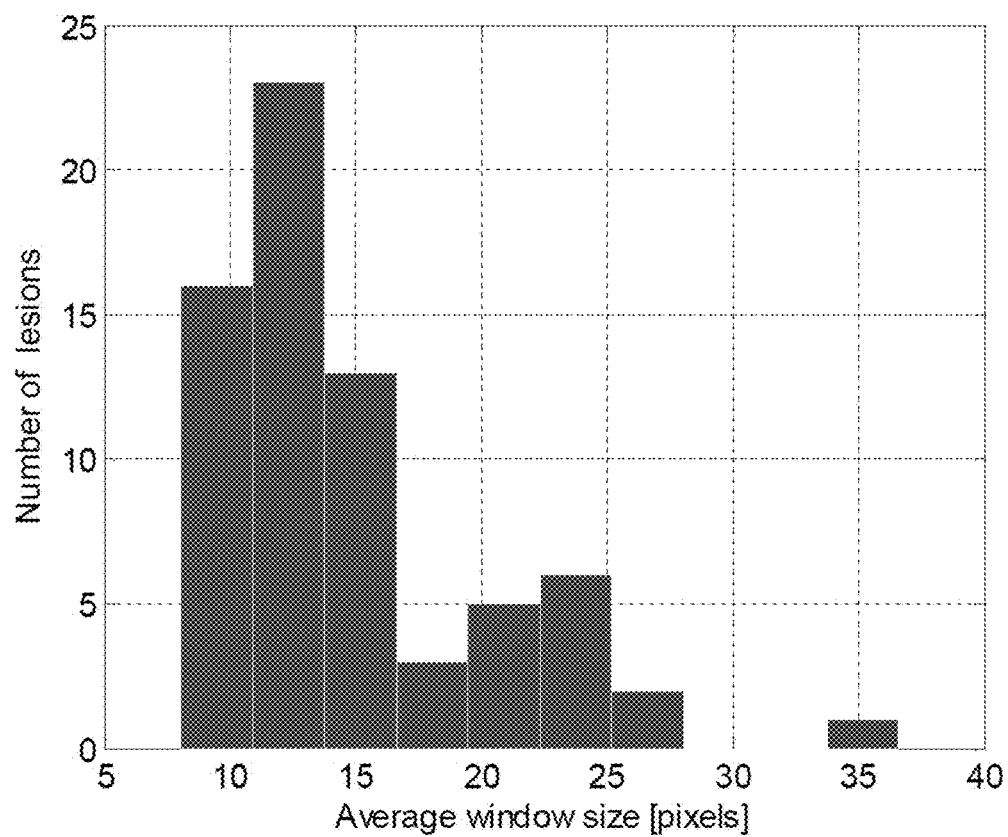
Figures 10A, 10B, 10C, 10D, 10E, 10F, 10G, 10H, 10I:
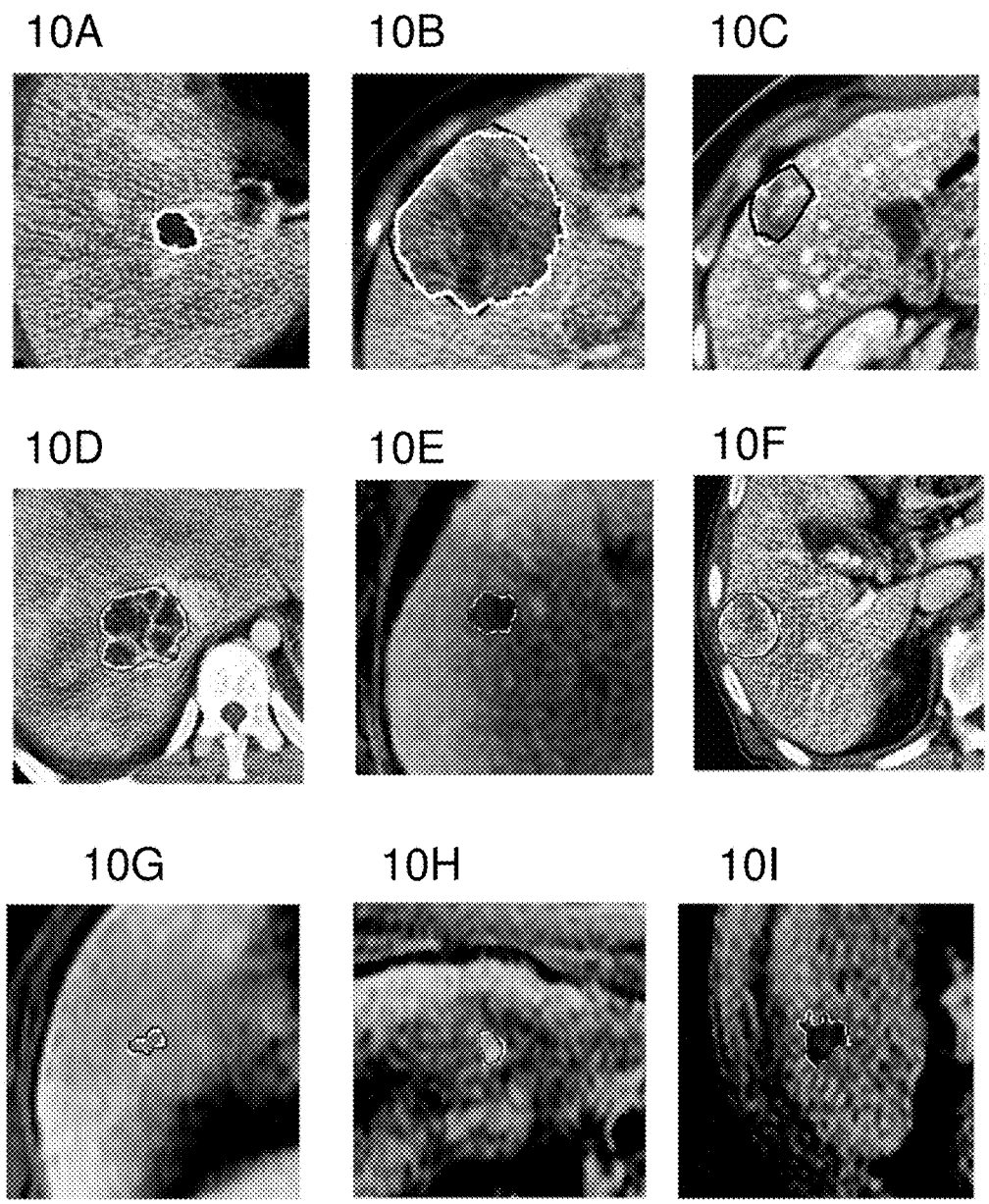
FIG. 10A through 10I is a set of images showing automatic segmentations of liver lesions using the present method. Piecewise constant model (PC) was applied.
Figure 11A:
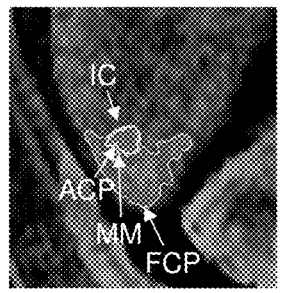
FIG. 11A through 11F is a set of images showing a comparison of the contours that were obtained by the manual marking (MM), the proposed ACP (adaptive contour parameters), the FCP method (fixed contour parameters) and the initial contour (IC)
Figure 11B:
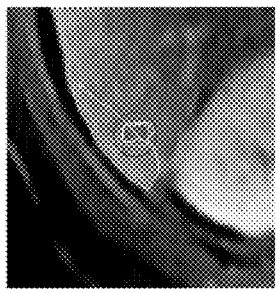
Figure 11C:
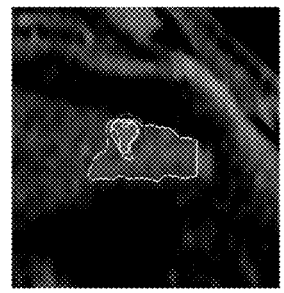
Figure 11D:
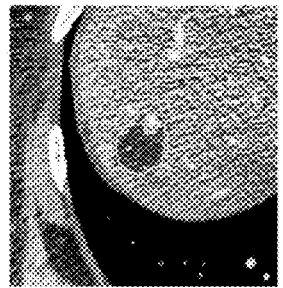
Figure 11E:
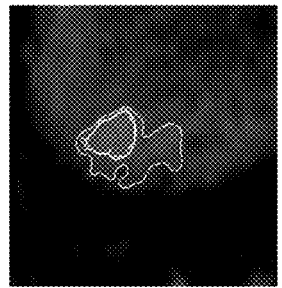
Figure 11F:
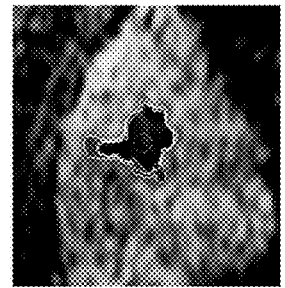

Example 1: The Contribution of an Adaptive Local Window for Level Set Segmentation Size Distribution of the Adaptive Local Windows FIG. 9A, 9B presents the distribution of the evaluated local window sizes for different lesions. The window sizes range between 5 and 19 pixels for MRI liver lesions and between 9 and 35 pixels for CT liver lesions. Therefore, choosing a single fixed-size region for all lesions may be inaccurate and cause an inevitable tradeoff during the segmentation process.

In order to isolate and analyze the contribution of the adaptive local window alone, cost function parameters of $\lambda_1=2$, $\lambda_2=2$ were chosen because they supplied the best average results for all 233 lesions. FIG. 10A-10I shows some examples of segmentation of different lesions. Shown are automatic segmentations (white) of liver lesions by using the presented method. Piecewise constant model (PC) was applied. (FIG. 10A, 10B) different lesions sizes, (FIG.

10C-10D) heterogeneous lesions, (FIG. 10E) homogeneous lesion, (FIG. 10F, 10G) low contrast lesions, (FIG. 10H, 10I) noisy background. MRI liver lesions—FIG. 10E, 10G-10I. CT images—FIG. 10A-10D, 10F. Black contours represent the manual annotations. Quantitative evaluation of the segmentation performance was conducted by calculating the Dice coefficient (Table I). This coefficient was calculated relative to the each radiologist's manual marking separately, then an average Dice was estimated. It is clear that the automated segmentation has high agreement with the manual markings for different local energies. Non-significant differences were found between the manual and the automated segmentations (Wilcoxon, p>0.05), thus the manual marking can be replaced by the automated one.

TABLE I

AVERAGE DICE COEFFICIENT AND 95% CONFIDENCE INTERVAL (CI) THAT WERE CALCULATED BETWEEN THE PROPOSED ALS AND EACH MANUAL MARKING

|  | ALW VS. Manual marking [95% CI] |
| --- | --- |
| PC energy | 0.89 [0.88, 0.90] |
| MS energy | 0.87 [0.86, 0.88] |
| HS energy | 0.88 [0.87, 0.89] |

Comparison with Fixed Square Local Window

Our Adaptive Local Window method (ALW) was compared with previous methods that utilize Fixed square Local Window (FLW) surrounding each contour point. The comparison was done for each of the 2 local energy models—Piecewise Constant (PC) and Mean Separation (MS). As was applied for our method, the same $\lambda_1=2$, $\lambda_2=2$ were chosen for FLW because they supplied the average best results for all 233 lesions. The only difference between the FLW and the ALS methods was the size of the local window in which the statistics were calculated. Hence, any difference in performance was directly related to the local window size. For FLW, we tested different fixed square windows in the range of 5 to 25 pixels, separately for MRI and for CT liver lesions. 10-pixels square window shows the average best performance for MRI liver lesions, while 14-pixels square window was the best for CT lesions, among other fixed window sizes. Therefore, those fixed sizes were used for latter ALW-FLW comparisons. For all 233 lesions, 10-pixels FLW showed an average Dice of 0.851 and 95% CI of [0.837 0.863] for all 3 local energies. Equivalent values of 0.832 and [0.814 0.846] were calculated for 14-pixels FLS.

Our ALW was significantly better than these FLW sizes (p<0.05, Wilcoxon) for each applied energy (Table I). This finding indicates the importance of adaptive local window. FIG. 11A-11G shows 7 different lesions and demonstrates the segmentation challenges. (FIG. 11A) PC model—CT liver lesion, (FIG. 11B) PC model—MRI liver lesion, (FIG. 11C) Mean separation (MS) model—MRI liver lesion, (FIG. 11D) Mean separation (MS) model—CT liver lesion. It suggests that the adaptive local window can handle diverse types of images better than local segmentation with fixed square window size. The superiority of the adaptive method can be seen for each internal energy—PC, MS.

Figure 12:
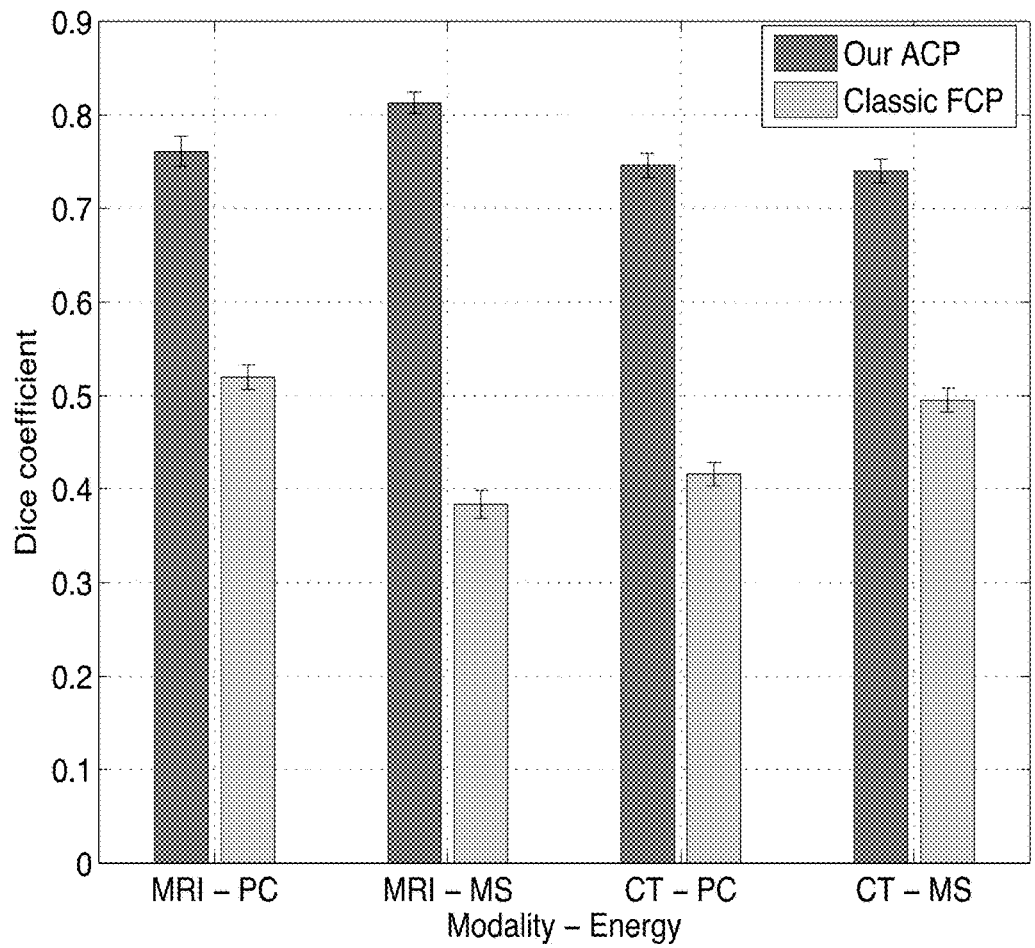
FIG. 12 is a bar graph comparing ACP and FCP methods in a subset of lesions, for which there was found more than 10% difference between the methods in a sense of agreement with the manual marking.
Figures 13A, 13B, 13C, 13D, 13E, 13F, 13G, 13H:
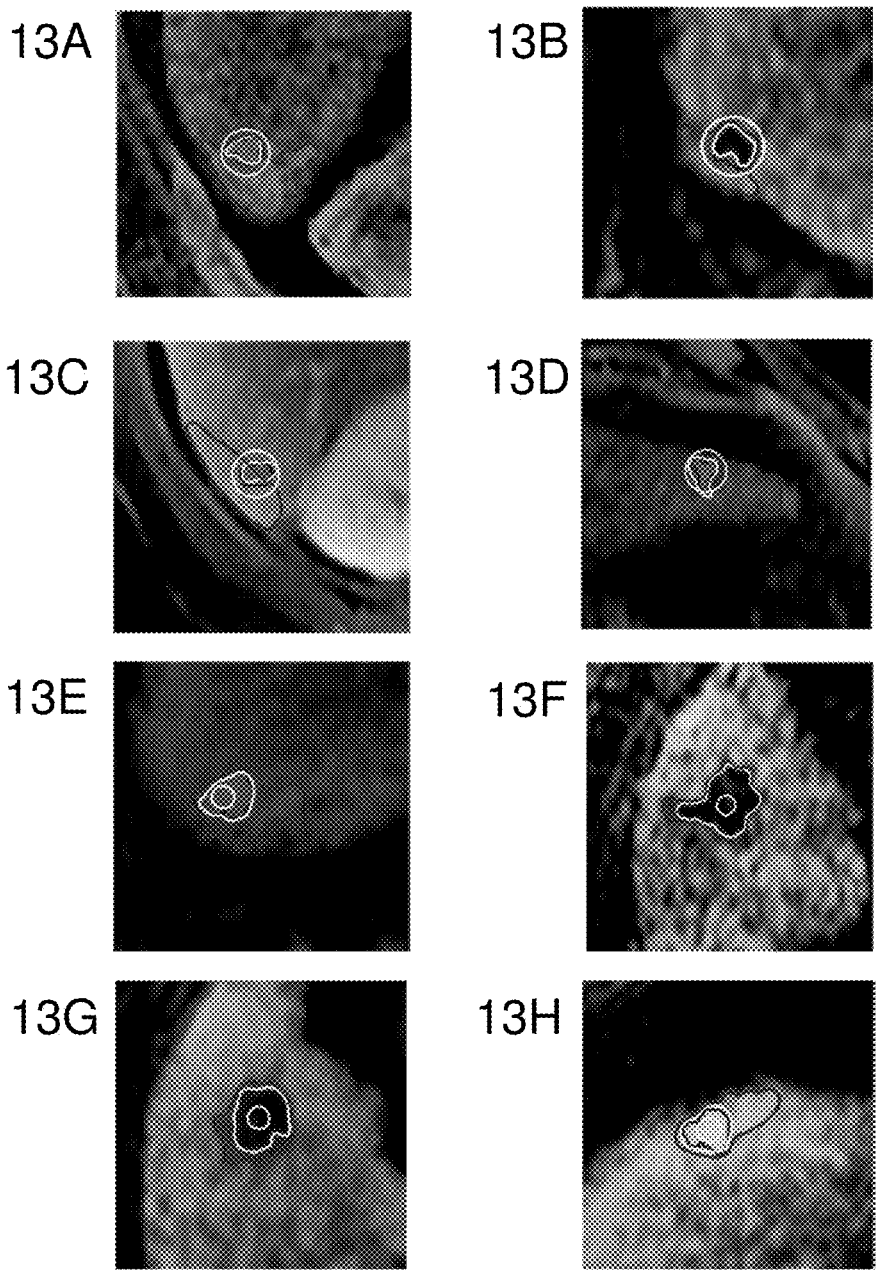
FIG. 13A through 13H is a set of images showing segmentation results by using different contour initializations (white circle). Manual marking (black contour), the present ALS method (white contour) and the FLS method (gray contour) are presented. Manual marking in general tracked the ALS closed curve (segmentation). The FLS was smaller than either curve.

The method's capabilities are demonstrated in a database of 233 diverse liver lesions imaged with either computed tomography or magnetic resonance imaging. The present method shows high agreement with the manual marking for a diverse dataset of CT and MRI images. A variety of spatial texture characteristics in the present datasets emphasize the strength of adaptive method. The described method can perform well with low contrast or heterogeneous lesions as, well as with noisy lesions or noisy background. In addition, The performance of our Adaptive Local Window method was compared to local state of the art frameworks that use predefined fixed-size square windows and fixed parameters of the energy functional. The results indicate that the present method outperforms these methods, especially with complex lesions such as low contrast lesions, heterogeneous lesions, or lesions with a substantially noisy background. It is almost impossible to choose single fixed-size local window or fixed parameters that can be best fitted to every case. Several subsets of lesions were also tested. Table II shows that for every lesion for which the absolute differences of the segmentation results between ALW and FLW were more than 10%, the present ALW was superior. Significant improvement of 0.234±0.101 was shown (Wilcoxon, p<0.001, for all three energy models). Another subset of lesions (FIG. 12), for which one or more automated methods obtained less than 70% agreement with the manual marking was also examined. The present ALW outperformed the FLW and showed significant improvement of 0.196±0.092 also for this set of lesions (Wilcoxon, p<0.05 for PC model, p<0.001 for MS and HS energies). As described here, other values can be developed according to image conditions.

TABLE II

ABSOLUTE PERFORMANCE DIFFERENCES HIGHER THAN 10% BETWEEN ALS AND FLS. DICE COEFFICIENT IS PRESENTED. WILCOXON PAIRED TEST WAS PERFORMED BETWEEN THE ALS AND EACH FLS

|  | Number of Lesions ALW [95% CI], FLW10 [95% CI] | Number of Lesions ALW [95% CI], FLW14 [95% CI] |
|---|---|---|
| PC | 11<br>0.82 [0.76, 0.88]<br>0.73 [0.66, 0.79] | 20<br>0.83 [0.78, 0.87]<br>0.73 [0.65, 0.79] |
| MS | 56<br>0.82 [0.78, 0.85]<br>0.62 [0.55, 0.67] | 58<br>0.84 [0.80, 0.86]<br>0.50 [0.44, 0.56] |
| HS | 25<br>0.82 [0.80, 0.85]<br>0.70 [0.65, 0.74] | 32<br>0.83 [0.78, 0.86]<br>0.69 [0.67, 0.74] |

Example 2: The Contribution of Adaptive Active Contours Parameters and Adaptive Local Window Together Six different contour initializations were created for MRI images, using radii of 3, 5, 7, 9, 11 and 13 pixels. Similarly, six different contour initializations were created for CT images, using radii of 5, 10, 15, 20, 25 and 30 pixels. For both MRI and CT images, these radii generated initial contours that were located inside the lesion ('small initialization'), while other contours were located close to the lesion boundaries ('accurate initialization'), and others were bigger than the lesion ('large initialization'). This broad range of initializations allowed us to evaluate the strength of our method in handling initial contours far away from the lesion in either direction.

Dice coefficient was calculated to evaluate the agreement of the automated segmentation with the manual marking. Wilcoxon statistical test was done because no prior knowledge regarding the data distribution should be assumed.

Segmentation Performance

All 276 lesions have been segmented by our proposed adaptive contour parameters method. For all 6 contour initializations, average Dice coefficients and standard errors of 0.78±0.05 and 0.79±0.05 were found for the PC and MS energies, respectively.

Several segmentation examples are shown in FIG. 15A-15C. In the left column is shown small initialization (3-pixels radius); middle column, more accurate initialization (5-pixels radius); right column, large initialization (9-pixels radius). FIG. 15A shows a low-contrast lesion, FIG. 15B shows lesions with heterogeneous surrounding region, FIG. 15C shows a noisy image region surrounding lesion, with lesion location close to the liver boundaries. White circle—initial contour, White contour—the presented segmentation, black contour—manual radiologist's annotation.

Comparison with Common-Used Local Level Set Method (Fixed Contour Parameters)

We compared our proposed method (ACP) with a state of the art local framework of level set segmentation. This framework uses Fixed $\lambda_1$, $\lambda_2$ Contour Parameters (FCP) and a fixed local window size. For our datasets, several values of $\lambda_1$ and $\lambda_2$ were tested, and $\lambda_1=\lambda_2=2$ was chosen. In addition, we used local window sizes of 5-pixels and 7-pixels surrounding each contour point for MRI and CT liver lesions respectively. Those fixed parameter values were selected for FCP because they supplied the average best results for all cases. For the combined dataset of 276 lesions and all six contour initializations, FCP had average Dice coefficients of 0.64±0.13 and 0.53±0.14 for PC and MS energy models, respectively. Those Dice coefficients were significantly lower (p<0.05 for PC and p<0.01 for MS, Wilcoxon) for FCP compared with our ACP segmentation performance. FIG. 13A-13H shows some examples of lesion segmentation for different initial contours.

Figure 14:
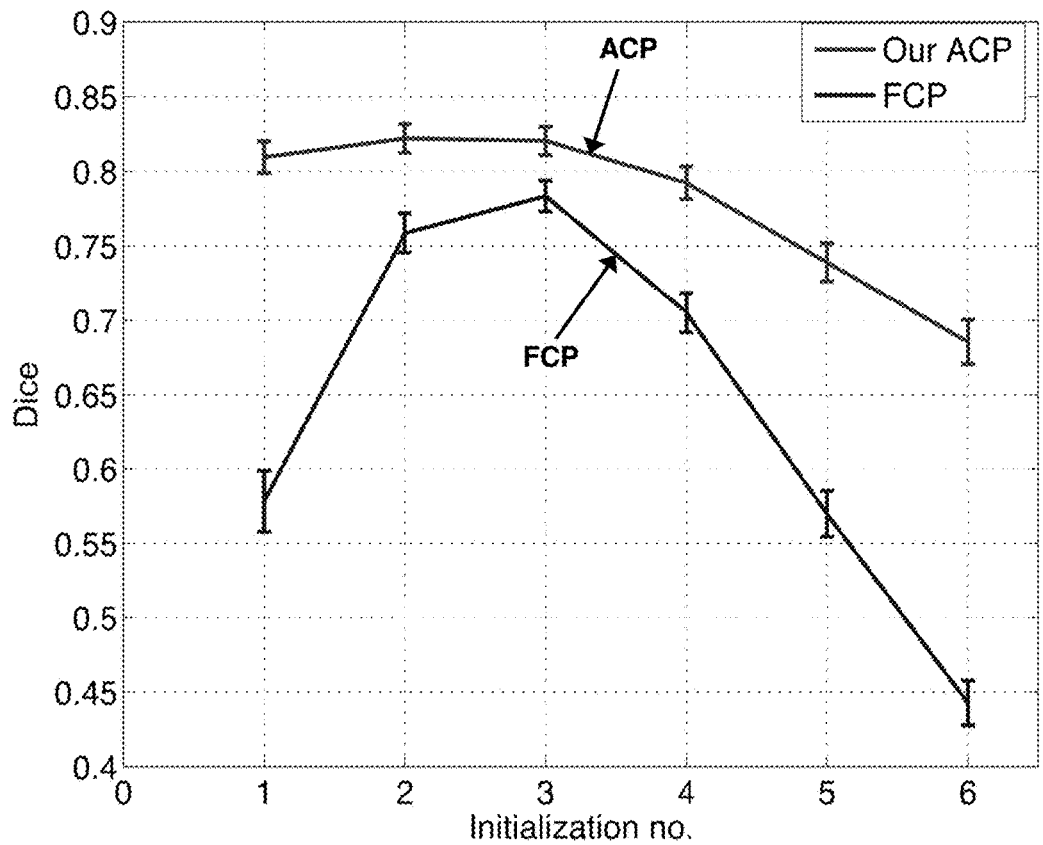
FIG. 14 is a graph showing dice coefficients (median±se), for different initializations of the level set contour.

A subset of lesions for which one or more automated methods obtained less than 85% agreement with the manual marking, indicating a more challenging case, was also examined (Table III). Across both datasets, both PC and MS models and all initializations, the average number of cases included in this subset was 103±24. For this subset, a significant Dice improvement of 0.21±0.09 was obtained using our ACP method, compared with the FCP (Wilcoxon, p<0.001). We also considered a subset of lesions where an absolute difference of more than 10% between our ACP and the FCP method was present; in these cases, ACP could be better or worse than FCP. This threshold was chosen based on a radiologist opinion that in our set of images, more than 10% difference is clinically significant. For this subset, ACP performed significantly better with a Dice improvement of 0.31±0.1 compared with FCP (p<0.001, Wilcoxon). Moreover, as can be seen in FIG. 14, the proposed ACP method again shows greater robustness to imaging modality and type of local energy modeled.

In addition to the comparisons with 2 level set frameworks, we also compared our ACP technique with 2 automatic, CNN-based segmentation methods. The first one is a patch based CNN technique in which a bounding box was created and the image was divided into 5×5 patches [21]. Each patch was classified by a neural network as normal or abnormal tissue (i.e., lesion). The bounding box size remained the same as the previous experiments for both the MRI and CT datasets. The architecture of the neural network replicated the fully connected layers of the CNN architecture we proposed for our ACP method. The learning rate ($\alpha=0.01$) and number of nodes (nodes=100) in the dense layer were optimized using Grid Search. Ten-fold cross validation was applied to evaluate the method. The patch-based CNN technique resulted in an average Dice coefficient of 0.48±0.27 for MRI liver lesions and 0.46±0.25 for CT lesions, significantly lower than the equivalent values obtained by our ACP method (Wilcoxon, p<0.001). The sensitivity of the method was 0.93 and the specificity 0.31, indicating that the network's low accuracy was primarily a result of false positives.

Example 3: Additional Datasets

Additional datasets have been analyzed and their average Dice coefficient was calculated (in brackets). The set includes 54 CT Ovarian tumors (0.866), 47 CT Kidney tumors (0.887), 42 CT Liver lesions (0.817), 24 colon tumors (0.818) and 552 pathologic lymph nodes (0.784).

Example 4: Systems for Carrying Out the Present Methods

As discussed above, the present methods are computer programmed to operate on the digital data contained in the image being characterized. The computer is programmed, e.g. using MATLAB to carry out the data manipulations that are used to characterize a region of interest in the image. Accordingly, the present invention comprises physical implementations of the described mathematic calculations and physical means to display the results that reveal the characterization of the region of interest in the digital image. A system for use with the present methods can include, for example, processor (e.g., processor), a data bus coupled to the processor (including a hard disk drive, etc., internally include data base); and a computer-usable medium (e.g., image processing unit constituting a computer-usable medium) embodying computer program code, the computer-usable medium being coupled to the data bus. The computer program code can include, for example, instructions executable by the processor and configured for identifying individual pixels in an image, as well as hand-markings made by an individual (e.g. radiologist) identifying a region of interest (e.g. a potential lesion) in the digital image. In still another embodiment, a processor-readable medium (e.g., data-processing system hard disk drive, etc.) storing computer code representing instructions to cause a process for identifying the region of interest by a marked boundary (segmentation).

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

REFERENCES

[1] T. Chan, L. Vese, Active contour without edges, IEEE Transaction on Image Processing 10 (2) (2001) 266-277.
[2] J. A. Yezzi, A. Tsai, and A. Willsky, A fully global approach to image segmentation via coupled curve evolution equations, J. Vis. Comm. Image Rep., vol. 13, no. 1, pp. 195-216, 2002.
[3] S. Lankton, A. Tannenbaum, Localizing region-based active Contours, IEEE Trans. Image Process. Vol. 17 (11) pp. 2029-2039, 2008.
[4] C. M. Li, C. Kao, J. Gore, Z. Ding, Implicit active contours driven by local binary fitting energy, in: IEEE Conference on Computer Vision and Pattern Recognition, 2007.
[5] C. Li, C. Kao, J. Gore, Z. Ding, Minimization of region-scalable fitting energy for image segmentation, IEEE Transactions on Image Processing 17, pp. 1940-1949, 2008.
[6] R. Malladi, J. A. Sethian, B. C. Vemuri, Shape modeling with front propagation: a level set approach, IEEE Transaction on Pattern Analysis and Machine Intelligence 17, pp. 158-175, 1995.
[7] Q. Zheng, Z. Lu, W. Yang, M. Zhang, Q. Feng, W. Chen, A robust medical image segmentation model using KL distance and local neighborhood information, vol. 43, no. 5, pp. 459-470, 2013.
[8] K. Zhang, H. Song, and L. Zhang, Active contours driven by local image fitting energy, Pattern Recognit., vol. 43, no. 4, pp. 1199-1206, 2010.
[9] L. Wang, J. Macione, Q. Sun, D. Xia, C. Li, Level set segmentation based on local Gaussian distribution fitting, Asian Conference on Computer Vision, pp. 293-302, 2009.
[10] D. Smeets, B. Stijnen, D. Loeckx, B. De Dobbelaer, P. Suetens, Segmentation of liver metastases using a level set method with spiral-scanning technique and supervised fuzzy pixel classification. 3D Segmentation in the Clinic: A Grand Challenge II—Liver Tumor Segmentation, 2008.
[11] S. Lankton, D. Nain, A. Yezzi, and A. Tannenbaum, Hybrid geodesic region-based curve evolutions for image segmentation, in Proc. SPIE: Med. Imag., vol. 6510, p. 65104U, 2007.
[12] J. An, M. Rousson, and C. Xu, Convergence approximation to piecewise smooth medical image segmentation, Proc. Med. Imag. Comput. Comp. Assist. Interven., vol. 4792, pp. 495-502, 2007.
[13] Q. Yang and D. Boukerroui. Optimal spatial adaptation for local region-based active contours: An intersection of confidence intervals approach. IMAGAPP, pp. 87-93, 2011.
[14] J Piovano and T. Papadopoulo. Local statistics based region segmentation with automatic scale selection. ECCV, pp. 486-499, 2008.
[15] B. N. Li, C. K. Chui, S. H. Ong, S. Chang, Integrating FCM and level sets for liver tumor segmentation. Proceedings of the 13th International Conference on Biomedical Engineering, pp. 202-205, 2009.
[16] Oliveira D A B, Feitosa R Q, Correia M M: Liver Segmentation using Level Sets and Genetic Algorithms. 4th Visapp. (2), pp. 154-159, 2009.
[17] C. Baillard, C. Barillot, and P. Bouthemy, "Robust adaptive segmentation of 3-D medical images with level sets," IRISA, Rennes Cedex, France, Res. Rep. 1369, November 2000.
[18] A. Bhattacharyya, On a measure of divergence between two statistical populations defined by their probability distributions, Bull. Calcutta Math. Soc., vol. 35, pp. 99-110, 1943.
[19] Hoogi A., Beaulieu C. F., Cunha G. M., Heba E., Sirlin C. B, Napel S., and Rubin D. L. Adaptive Local Window for Level Set Segmentation of CT and MRI Liver Lesions. preprint arXiv: 1606.03765, 2016.
[20] Haralick, R. M., Shanmugam K. and Dinstein I., Textural Features for Image Classification, IEEE Transactions on Systems, Man and Cybernetics, SMC vol. 3, no. 6, pp. 610-620, 1973.

[21] A. Krizhevsky, I. Sutskever and G. E. Hinton. ImageNet Classification with Deep Convolutional Neural Networks. Advances in Neural Information Processing Systems, 2012.

[22] X. Glorot and Y. Bengio, "Understanding the difficulty of training deep feedforward neural networks," in Proc. AISTATS, pp. 249-256, 2010.

[23] G. E. Hinton, N. Srivastava, A. Krizhevsky, I. Sutskever, and R. R. Salakhutdinov. Improving neural networks by preventing co-adaptation of feature detectors. arXiv preprint arXiv:1207.0580, 2012.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A computer-implemented method for characterizing a feature of interest in a digital image, using an adaptive local window, comprising the steps of:
   (a) obtaining an initial contour for a feature of interest, the initial contour formed of contour points;
   (b) defining a region of interest around the contour; and
   (c) segmenting the feature of interest by iteratively selecting a size of a local window surrounding each point on the contour, wherein the local window size is determined based on (i) homogeneity, (ii) contrast surrounding each contour point, (iii) approximate lesion size, and (iv) an energy function, wherein the energy decreases as the segmenting progresses.

2. The method according to claim 1, wherein the initial contour is represented as an initial zero level set.

3. The method according to claim 2, wherein selecting a size of a local window comprises calculating spatial statistics only for pixels that are within a narrow range 10 pixels of the zero set level.

4. The method according to claim 1, wherein the region of interest has a shape selected from the group consisting of: a square, a rectangle, a circle, and an oval.

5. The method according to claim 1, wherein the energy function comprises a calculation of a mean-curvature flow-like evolving the active contour.

6. The method according to claim 1, wherein a smaller local window is used when contrast in the digital image is low, a larger local window is used when the digital image contains a high level of noise or heterogeneity, or both.

7. The method according to claim 1, wherein the segmenting stops automatically at a set degree of convergence between iterations.

8. The method according to claim 1, wherein the feature of interest is a lesion in a digital medical image.

9. The method according to claim 8, wherein the digital medical image is selected from the group consisting of: a magnetic resonance imaging (MRI) image, a computerized tomography (CT) scan, a mammogram, and an X-ray image.

10. The method according to claim 1, wherein step (c) is automated.

11. A system, comprising:
    a processor, and
    a non-transitory computer readable medium comprising instructions that cause the system to perform one or more steps of claim 1.

12. A computer-implemented method for characterizing a feature of interest in a digital image, using a calculated adaptive level set method, comprising:
    (a) obtaining an initial contour for a feature of interest; and
    (b) producing an evolved contour towards the boundary of the feature of interest, wherein the producing comprises determining weighting parameters of a level set function using a convolutional neural network (CNN), wherein the weighting parameters are determined based on:
        output probabilities from the CNN that are probabilities of the initial contour being inside the feature of interest and far from its boundaries, outside the feature of interest and includes it and far from its boundaries, or close to a boundary of the feature of interest;
    wherein the weighting parameters control the direction and magnitude of contour evolution,
    to characterize the feature of interest.

13. The method according to claim 12, wherein the weighting parameters are calculated using a formula considering probabilities of:
    (a) inside the feature of interest and far from its boundaries (p1);
    (b) outside the feature of interest and includes it and far from its boundaries (p3);
    (c) close to a boundary of the feature of interest (p2), wherein
    if p3>p1 the contour shrinks, if p1>p3, the contour expands, and p2 acts as a stabilizing factor.

14. The method according to claim 13, wherein the CNN comprises two convolutional blocks, followed by two dense layers, including a final three-node layer.

15. The method according to claim 12, wherein the CNN uses raw images as feature maps.

16. The method according to claim 12, wherein the CNN comprises a filter bank layer that convolves each input feature map with a set of learned weights/filters.

17. The method according to claim 12, wherein the CNN comprises a non-linear activation applied to the output of the filter layer to obtain features that are non-linear transformations of the input.

18. The method according to claim 12, wherein the feature of interest is a lesion in a digital medical image.

19. The method according to claim 12, wherein the digital medical image is selected from the group consisting of: a magnetic resonance imaging (MRI) image, a computerized tomography (CT) scan, a mammogram, and an X-ray image.

20. A system, comprising:
a processor, and
a non-transitory computer readable medium comprising instructions that cause the system to perform one or more steps of claim 12.

* * * * *